(12) United States Patent
Cheng et al.

(10) Patent No.: US 6,448,794 B1
(45) Date of Patent: Sep. 10, 2002

(54) APPARATUS AND METHOD FOR HIGH THROUGHPUT ELECTROROTATION ANALYSIS

(75) Inventors: Jing Cheng, Beijing; Junquan Xu, Fujian; Xiaoshan Zhu, Hubei; Litian Liu, Beijing, all of (CN); Xiao-Bo Wang; Lei Wu, both of San Diego, CA (US)

(73) Assignee: Aviva Biosciences Corporation, San Diego, CA (US)

( * ) Notice: Subject to any disclaimer, the term of this patent is extended or adjusted under 35 U.S.C. 154(b) by 0 days.

(21) Appl. No.: 09/643,362

(22) Filed: Aug. 22, 2000

(30) Foreign Application Priority Data

Mar. 15, 2000 (CN) .......................................... 00104350
Aug. 18, 2000 (CN) .......................................... 00124086

(51) Int. Cl.⁷ ...................... G01R 27/08; G01R 31/08; G02F 1/133; G01N 33/53
(52) U.S. Cl. ...................... 324/693; 324/692; 324/521; 324/515; 349/33; 436/806
(58) Field of Search ...................... 324/750, 514, 324/521, 622, 86, 692, 631, 107, 770, 693; 349/141, 33; 204/547; 436/806, 807

(56) References Cited

U.S. PATENT DOCUMENTS

| | | | |
|---|---|---|---|
| 3,975,085 A | * 8/1976 | Yamada et al. | ............... 349/33 |
| 4,626,506 A | 12/1986 | Arnold et al. | |
| 4,634,669 A | 1/1987 | Arnold et al. | |
| 4,794,089 A | 12/1988 | Mroczkowski et al. | |
| 4,801,543 A | 1/1989 | Arnold et al. | |
| 6,056,861 A | * 5/2000 | Fuhr et al. | ................... 204/547 |

FOREIGN PATENT DOCUMENTS

GB    WO 93/16383    8/1993
WO    WO 98/29732    7/1998

OTHER PUBLICATIONS

Becker H and Manz A, in: Sensors Update, vol. 3, editors: Baltes H, Gopel W. and Hesse J, VCH Weinheim, pp 209–238 (1998).
Fuhr et al., *Stud. Biophys.* 108: 149–164, No. 3 (1985).
Baumann, et al. "Microelectronic sensor system for microphysiological application on living cells," *Sensors and Actuators B*, 55:77–89, Apr. 25, 1999.
Pethig, et al., "Development of biofactory–on–a–chip technology using excimer laser micromachining," *J. Micromech. Microeng.* 8:57–63, 1998.
Arnold & Zimmermann, *Z. Naturforsch.*, 37c:908–915, (1982).

(List continued on next page.)

*Primary Examiner*—N. Le
*Assistant Examiner*—Anjan K. Deb
(74) *Attorney, Agent, or Firm*—Knobbe, Martens, Olson & Bear, LLP

(57) ABSTRACT

The present invention concerns a high throughput electrorotation chip having an array of electrorotation units and methods of use thereof. To make the high throughput electrorotation chip, a plurality of electrorotation units (EU) are fabricated on a substrate or support and each EU is capable of producing a rotating electric field upon the application of an appropriate electrical signal. Exemplary embodiments include a row-column configuration of EUs having four electrode elements realized through two conductive-layers. The electrode elements may be linear, concave, or convex. Thin plates having one or multiple holes are bound to high-throughput electrorotation chips to form assay chambers having one or multiple wells. Particles can be introduced to the wells and electrorotation measurements can be performed on the particles. The high throughput electrorotation chip and chamber may be used for cell-based screening for leading drug candidate molecules from a compound library, for high-throughput characterizing particle electric properties, and for high-throughput assaying molecular compositions of unknown solutions.

12 Claims, 20 Drawing Sheets

OTHER PUBLICATIONS

De Gasperis et al., *Meas. Sci. Technol.* 9: 518–529, 1998.

Delmarche, E. et al., *J. Am. Chem. Soc.*, 120: 500–508. (1998).

Effenhauser, C.S., et al., *Anal. Chem.*, 69:3451:3457, (1997).

Fullon R. J. et al, *Clinical Chemistry*, 43:1749–1756, (1997).

Gascoyne et al., *Bioelectrochem. Bioenerg.* 36:115–125 (1998).

Gimsa et al., in *Physical characterization of biological cells*, Schutt W, Klinkmann H and Laprecht I and Wilson T editors, Gesundheit, Berlin, pp. 295–323, (1991).

Huang et al., *Biochim. Biophys. Acta* 1282:76–84, (1996).

Huang Y., et al., *Biochim. Biophys. Acta* 1417:51–62 (1999).

Huang et al., *Phys. Med. Biol.*, 37:1499–1517, (1992).

Kopp, et al., Current opinion in Chem. Biol., 1:410–419, (1997).

Manz, A. and Becker H., editors, *Microsystem technology in Chemistry and Life Science*, Topics in Current Chemistry, 194, Spring Heidelberg, (1998).

Simpson PC, Roach D, Woolley AT, Thorsen T, Johnston R, Sensabaugh GF, Mathies RA, *Proc. Natl. Acad. Sci., USA*, 95:2256–2261 (1998).

Wang X–B, at al., *Biochim. Biophys. Acta.* 1193:330–334, (1994).

Yang et al., *Biophys. J.*, 76:3307–3314 (1999).

\* cited by examiner 322 324 320 328 326

APPARATUS AND METHOD FOR HIGH THROUGHPUT ELECTROROTATION ANALYSIS

This application claims priority under 35 U.S.C. §119(a) to Chinese Application No. 00104350.1, entitled APPARATUS AND METHOD FOR HIGH THROUGHPUT ELECTROROTATION ANALYSIS, filed on Mar. 15, 2000 and Chinese Application No. 00124086.2, entitled APPARATUS AND METHOD FOR HIGH THROUGHPUT ELECTROROTATION ANALYSIS, filed on Aug. 18, 2000.

FIELD OF THE INVENTION

The present invention concerns the field of electrorotation and biophysics. More specifically, embodiments include micromachined or microfabricated electrorotation chips, which produce a rotating electric field and can evaluate the electrorotation behavior of biological and non-biological particles; an apparatus for analyzing the electrorotation properties of such particles; and methods of use thereof.

BACKGROUND OF THE INVENTION

Modern biotechnological and pharmaceutical approaches use a variety of analytic techniques to ascertain the behavior or identity of a molecule, cell, or biological particle. For example, investigators frequently use microbead-based multiplexed assays for analyzing the types and concentrations of target molecules in an "unknown" solution (see, e.g., Fulton R. J. et al, *Clinical Chemistry*, 43:1749–1756, (1997)). The target molecules may include antigens, antibodies, oligonucleotides, receptors, peptides, or enzyme substrates and may be labeled with a reporting molecule (e.g., a fluorescent molecule). Typically, in such an assay, different types of microbeads are used. Each type of microbead can be distinguished from others based on physical and chemical properties such as color, size, fluorescence molecule types and fluorescence intensity. The surfaces of different types of microbeads containing different types of molecules, i.e., each type of microbead is surface-activated or coated with one type of molecule. The molecules coating the surface of the microbeads may also be antibodies, antigens, oligonucleotides, receptors, peptides, enzyme substrates. Ideally, each molecule coating the surface of the microbeads interacts with one class of target molecule in the "unknown" solution.

Next, the surface-coated microbeads of many types are mixed together and are incubated with the "unknown" solution to allow the target molecules from the "unknown" solution to interact with the immobilized molecules on the microbeads. Prior to the incubation, all the target molecules are pre-labeled with certain types of reporter molecules (e.g., fluorescent molecules). Following the incubation, the detection of the reporter bound to the different types of microbeads is performed. By one approach, flow cytometry is used to analyze the levels of fluorescence on the individual microbeads and also determine the type of microbead detected. Because a "one-to-one" correspondence between the labeled target molecule and the immobilized molecule can be made, the identity and concentration of the target molecule in the "unknown" solution can be determined. A high-throughput format is desirable for these assays to expedite the analysis.

Modern approaches to pharmaceutical development also involve the analysis of interactions between a target molecule and molecules, cells, or particles of interest. For example, cell-based techniques are frequently used to screen chemical compound libraries for new drugs. The screening process typically employs cells having a target molecule to which an interaction with a drug-candidate is sought. The target molecule-containing cells are loaded into different reaction wells and are exposed to chemical compounds from a compound library. The cells are incubated with the chemical compounds for a specified time and then are evaluated for an interaction between the chemical compound and the target molecule. The detection of the interaction can be accomplished in many ways and fluorescence-based systems are frequently used. A similar assay determines the response of specific cell types to various amounts of chemical compounds and times of exposure. This type of assay can also be performed with a fluorescence-based detection system but the experimental set up allows for the determination of quantitative information. Desirably, a high-throughput system is also used for these assays to expedite drug development. The present invention relates to biological analyses which utilize electrorotation to characterize the behavior or identity of a molecule, cell or particle. Electrorotation analyses involve observing the behavior of molecules, cells, and particles, as well as complexes of these materials in a electric field that is applied so as to cause a rotation of the studied material. "Electrorotation" is a term of art that refers to the rotation of a material in an electric field. When a material is subjected to a rotating field, it becomes electrically polarized and the induced polarizations interact with the applied rotating fields, which produces a rotating torque that drives the rotation of the material. The rotation behavior (e.g., rotation rate and direction) depends on the frequency of the rotating field and electrical properties that are specific for the material being rotated. The measurement of rotational behavior can be expressed as a function of the frequency of the applied rotating field. From these measurements, the electrical properties (e.g., electrical conductivity and permittivity) unique to the material can be derived.

A number of electrorotation-based techniques have been developed for distinguishing particle types and analyzing particle properties. For example, U.S. Pat. No. 4,626,506 discloses an approach to distinguish cells that are secreting a cellular substance (e.g., proteins, hormones, etc) from non-secreting cells in the suspension. Further, U.S. Pat. No. 4,634,669 discloses an approach to differentiate two groups of particles based on observing different rotating directions of the particles when the frequencies of the applied rotating field are varied. Still further, U.S. Pat. No. 4,801,543 discloses an approach to analyze different groups of particles based on exposing the particles to two superimposed, simultaneous rotating electrical field forces with opposite rotation directions. Additionally, International Publication No. WO 93/16383 discloses an approach for detecting target molecules, which involves forming a complex between micro-particles and a target species and observing the difference in electrorotation properties between the original micro-particles and the complexes.

More discussion of electrorotation and its uses can be found in, for example, Arnold & Zimmermann, *Z. Naturforsch.*, 37c:908–915, (1982); Fuhr et al., *Stud. Biophys.* 108: 149–164, (1985); Gimsa et al., in *Physical characterization of biological cells*, Schutt W, Klinkmann H and Laprecht I and Wilson T editors, Gesundheit, Berlin, pp 295–323, (1991a); Huang et al., *Phys. Med. Biol.*, 37: 1499–1517, (1992); Huang et al., *Biochim. Biophys. Acta* 1282:76–84, (1996); Wang et al., *Biochim. Biophys. Acta.* 1193: 330–344, (1994); Gascoyne, Becker FF and Wang, *Bioelectrochem. Bioenerg.* 36: 115–125, (1998); and Huang Y, et al., *Biochim. Biophys. Acta* 1417: 51–62 (1999).

BRIEF SUMMARY OF THE INVENTION

The present invention concerns the manufacture and use of electrorotation chips and an apparatus for high-throughput analysis of many different types of particles. Advantageously, embodiments can be used for high-throughput analysis of the rotation behaviors of different particle types on a single electrorotation chip, which allows for a rapid determination of the electrical properties of many different particles. Embodiments can also be used for high-throughput analysis of molecule-molecule, molecule-particle, and particle-particle interactions. For example, the invention can be used for cell-based, high-throughput screening for potential drug molecules from a chemical compound library.

Embodiments include an electrorotation chip comprising a substrate and a plurality of electrorotation units disposed on said substrate, wherein each of said electrorotation units comprises a plurality of electrode elements that are positioned on said substrate such that a rotating electrical field is generated when a plurality of phase-shifted electrical signals are applied to said electrode elements. This electrorotation chip can have a substrate that comprises a material selected from the group consisting of a non-porous solid material, and a porous solid material. This non-porous solid material or said porous solid material can be selected from the group consisting of glass, silicon, plastic, and ceramic. Some embodiments also have electrorotation units that are distributed in a plurality of columns and rows. Other embodiments have a plurality of electrode elements that are positioned such that the rotating electrical fields generated by adjacent electrorotation units are in opposite directions. More embodiments have a plurality of electrode elements that are positioned such that an electrode element of a first electrorotation unit is electrically connected to the nearest electrode element of a second adjacent electrorotation unit.

The electrorotation chip described above can also have a plurality of electrode elements that are positioned such that an electrode element of a first electrorotation unit is also an electrode element of a second adjacent electrorotation unit. The electrorotation chip described above can further comprise at least one signal generator that generates the phase-shifted electrical signals, said at least one signal generator being electrically connected to said electrorotation units. This signal generator can generate a periodic waveform in some embodiments. In some embodiments, the phase-shifted electrical signals are generated using a plurality of analog filters to shift the phase of a signal. Further, in some embodiments N is the number of said electrode elements in each said electrorotation unit and the phase-shifted electrical signals have phase offset values of 0, 360/N, 360*2/N, 360*3/N, 360*(N−1)/N. The electrorotation chip described above can also comprise a plurality of switches that apply the phase-shifted electrical signals to said electrode elements when said switches are conducting. These switches can be selected from the group consisting of bipolar junction transistors and metal oxide semiconductor field-effect transistors.

In other embodiments, the electrode elements resemble a structure selected from the group consisting of a butterfly footprint, a rectangular shape, and one face shaped in an arc. The electrorotation chip can have electrorotation units that comprise at least three electrode elements uniformly disposed about a center of the rotating electric field. Some electrorotation chips have electrorotation units that comprise four electrode elements uniformly disposed about a center of the rotating electric field. Some electrorotation chips also have a plate joined to said electrorotation chip, wherein said plate comprises at least one hole. This plate can comprise a plurality of holes and, each of said holes can provide access to only one electrorotation unit.

Another aspect of the invention concerns an electrorotation device comprising a plurality of signal inputs each of said signal inputs receiving a signal which is shifted in phase from signals received by the other signal inputs, wherein each signal input is electrically connected to a plurality of electrode elements, said electrode elements being organized into a plurality of electrorotation units, each electrorotation unit comprising at least one electrode element electrically connected to each of said signal inputs, and wherein when said phase-shifted signals are applied to said electrode elements in said electrorotation units a rotating electric field is produced in said electrorotation units. This electrorotation device can be modified to have a plurality of electrode elements that are electrically connected to each signal input are electrically connected to one another. The plurality of electrode elements can also be positioned such that the rotating electrical fields generated by adjacent electrorotation units are in opposite or same directions. In many embodiments, the electrorotation device described above have electrorotation units that are disposed on a substrate. The electrode elements can be electrically connected to a signal input and can be electrically insulated from the electrode elements connected to other signal inputs.

In other embodiments, a plurality of electrode elements are electrically connected to one another and to each signal input by conductors, and the conductors between electrode elements, which are electrically insulted from one another, are distributed between at least two layers in said substrate. In some aspects of this electrorotation chip, the electrode elements are positioned such that an electrode element of a first electrorotation unit is also an electrode element of a second adjacent electrorotation unit. In other aspects of this embodiment, phase shifted signals provided by said signal generators may be selectively applied to said electrorotation units. This embodiment can also comprise switches that are disposed between said signal generators and said electrode elements such that said phase-shifted signals are applied to said electrode elements in said electrorotation units when said switches are conducting. These switches can be selected from the group consisting of bipolar transistors and metal-oxide-semiconductor-field-effect-transistors (MOSFETs). In some embodiments, a single signal generator generates said plurality of phase-shifted signals which are applied to said signal inputs and, in other embodiments, the phase difference between said plurality of phase-shifted signals is 360°/N where N is the number of electrode elements in each electrorotation unit.

Methods of the invention include, for example, a method of determining an electrical property of a particle comprising the steps of providing an electrorotation chip that comprises a substrate having a plurality of electrorotation units disposed thereon; placing at least one particle in said plurality of electrorotation units; inducing rotating electrical fields in said electrorotation units; and measuring the rotation of said at least one particle and thereby determining the electrical property of said at least one particle. In some aspects of this method, the particle is selected from the group consisting of a biological molecule, a biological complex, an immune complex, a liposome, a protoplast, a platelet, a virus, and a cell. hi other aspects, the rotation of said at least one particle is measured at more than one frequency. Desirably, the electrical properties of a plurality of particles are measured and said plurality of particles can be a heterogeneous population. The method above can further comprise identifying those particles that have similar electrical properties.

Another approach described herein involves a method of identifying an agent that changes the electrorotational properties of a cell comprising the steps of providing an electrorotation chip that comprises a substrate having a plurality of electrorotation units disposed thereon; placing at least one cell in said plurality of electrorotation units; contacting said cell with a candidate molecule; inducing rotating electrical fields in said electrorotation units; measuring the rotation of said cell; determining the presence or absence of an effect on the electrorotational properties of said cell by comparing the rotation of said cell before contact with said candidate molecule with the rotation of said cell after contact with said candidate molecule or by comparing the rotation of a control cell that was not exposed to said candidate molecule with the rotation of said cell after contact with said candidate molecule; and identifying said candidate molecule as an agent that changes said electrorotational properties of said cell if said cells contacted with said candidate molecule have different electrorotational properties than said cells before contact with said candidate molecule or said control cells. In some aspects of this method, rotation is measured at more than one frequency and the electrical property of a plurality of cells can also be measured. Additionally, the plurality of cells can be a heterogeneous population and the method can further comprise identifying those cells that have similar electrical properties.

Another method involves an approach to determine the identity or concentration of a molecule in a biological sample. Thus methode comprises the steps of providing an electrorotation chip that comprises a substrate having a plurality of electrorotation units disposed thereon; coating particles with a detection reagent which binds to said molecule; placing at least one coated particle in said plurality of electrorotation units; contacting said coated particles with said biological sample; applying an electrical signal to said electrorotation units; measuring the rotation of said coated particles; and determining the identity or concentration of said molecule in said biological sample by comparing the rotation of coated particles contacted with said biological sample with coated particles that have not been contacted with said biological sample. In some aspects of this method, the detection reagent is selected from the group consisting of a dye, an antibody, and a ligand.

DETAILED DESCRIPTION OF THE INVENTION

Figure 1:
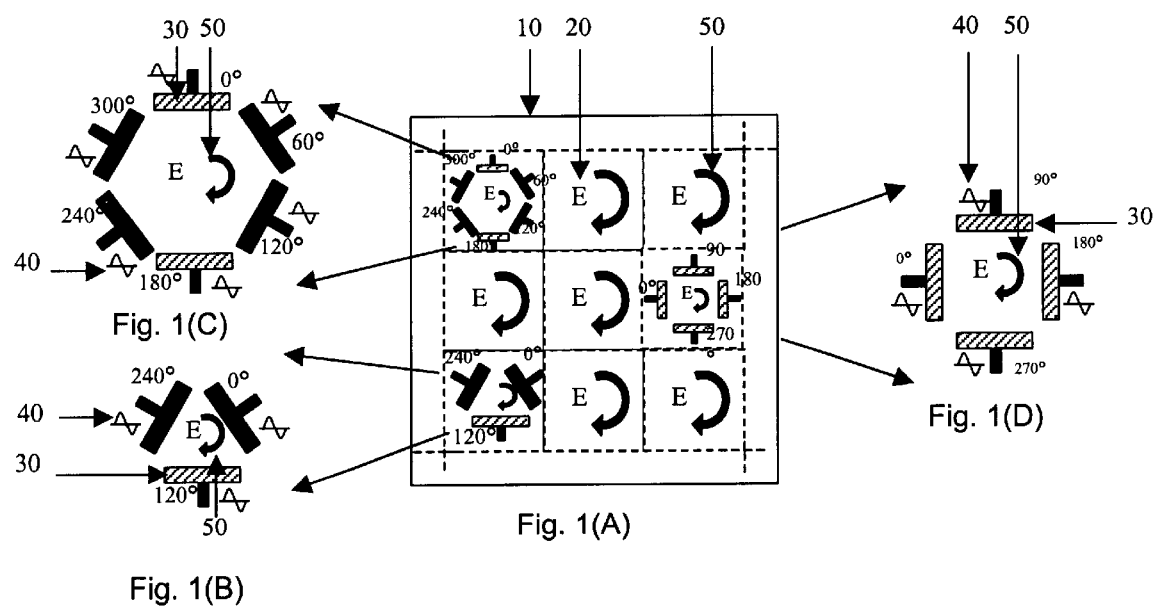
FIG. 1(A) is a schematic diagram showing a high-throughput electrorotation assay chip.
FIG. 1(B) is an electrorotation unit with 6 electrodes.
FIG. 1(C) is an electrorotation unit with 3 electrodes.
FIG. 1(D) is an electrorotation unit with 4 electrodes.

Aspects of the present invention concern the fabrication and use of a device that allows for high throughput electrorotation analysis of a variety of particles on the same electrorotation chip. Because the embodied electrorotation chip comprises a plurality of electrorotation units (EU), multiple samples can be analyzed under the same or very similar experimental conditions. In contrast, when multiple samples are introduced onto EUs on different electrorotation chips, the experimental conditions can vary from chip to chip leading to unreliable results. Advantageously, several of the embodiments described herein maintain substantially identical experimental conditions for each electrorotation analysis by virtue of the fact that the embodied electrorotation chips contain a plurality of EUs on the same chip.

The rotating electrical field is produced by applying phase-shifted signals to electrode elements. The EUs may be distributed in columns and rows for ease of fabrication. The shape and placement of the electrode elements and the amplitude, frequency, and waveform of the signal are factors in determining the characteristics of the electrical field.

The shape of the electrode elements may be varied to produce different electrical fields. Examples of electrode element shapes include butterfly, rectangular and arcuate shapes. Usually, at least three electrode elements are uniformly spaced about the center of the EU, although the number of elements and spacing may vary.

The electrical field may also be affected by neighboring EUs. Thus, in some embodiments, the cross-talk effect is reduced by connecting each signal input to a plurality of electrode elements which are electrically connected to one another. In some embodiments, alternating the direction of rotation of neighboring EUs further helps to minimize the cross-talk effect.

Some electrorotation chip embodiments described herein comprise multiple EUs disposed on a support (e.g., a chip) so as to allow for analysis of the electrical properties of a plurality of homogeneous or heterogeneous particles, cells, or molecules in a single assay. In general, the electrorotation chips described herein comprise a support or substrate and a plurality of EUs disposed on said support. By the term "support" is meant a macromolecular structure. Desirable supports are composed of a porous or nonporous solid material. Preferred supports include, for example, glass, silicon, plastic, and ceramic.

The phase-shifted signals are generated by a signal generator, which may be integrated as part of the chip or connected externally. A digital or analog signal generator could be used to produce a waveform, and phase-shifting filters could then produce the phase-shifted signals. Alternatively, a signal generator could be used to directly generate multiple phase-shifted signals.

The phase offsets are preferably uniformly spaced. Thus an EU with N electrode elements would have phase offsets spaced at 360/N degrees. The offsets could be increased so that the total number of degrees is a multiple of 360 (e.g., 720, 1080, or 1440). Non-uniform phase offsets can also be used to produce the rotating electric field.

Periodic waveforms such as sinusoids, square-waves and ramp waveforms are typically used, although non-periodic or irregular waveforms may also be used.

In some embodiments, it may be desirable to induce a rotating electrical field in only one or a group of EUs, instead of the entire array. Switches such as bipolar junction transistors (BJTs) or metal oxide semiconductor field effect transistors (MOSFETs) may be used to selectively energize the EUs.

The embodied electrorotation chips can be used to analyze the electrical properties of a variety of particles in an array format. By one approach, for example, multiple samples are delivered to the individual electrorotation chamber units with sample dispensing heads. A rotating electrical field is induced and the rotation of the particles is monitored at individual electrorotation units one after another or several units may be run simultaneously. When a charge coupled device (CCD) camera with large detection window is used, for example, the electrorotation responses of particles in several electrorotation units can be monitored simultaneously. A large variety of particles of many shapes and sizes can be analyzed using an embodiment described herein including, but not limited to, biological molecules, biological complexes, immune complexes, liposomes, protoplasts, platelets, virus, cells, and microbeads. By using these embodiments, one of skill can rapidly analyze the electrical properties of a plurality of particles and monitor how the particles respond to changing environmental stimuli.

In addition to monitoring the electrical properties of homogeneous and heterogeneous populations of particles, embodiments described herein can also be used to rapidly identify particles that have similar electrical properties. As defined here and throughout this application, "particle" refers to any solublized or suspended matter of any shape in a fluid. Particles can be biological or non-biological, including, but not limited to, cells, bacteria, virus, DNA molecules, proteins, microbeads (e.g., metallic, plastic, glass, polystyrene beads, or beads of complex compositions), and nanobeads. Preferably, cells and/or cells complexed with a ligand (e.g., antibody, peptide, or chemical) that may or may not be joined to a particle are analyzed by an embodiment described herein. Once particles with similar electrical properties are identified, they can be grouped or classified according to these electrical properties. Further, the identification of particles with similar electrical properties can be exploited to classify cells that are actively producing a cellular substance, such as a protein, carbohydrate, or lipid. This identification process is preferably performed on a heterogeneous population of cells (e.g., only some of the cells produce the cellular substance). To facilitate the analysis, a marker (e.g., an antibody, bead, carrier, or other ligand) which confers a change in electrical properties when bound to a cell can be used to bind to cells that are actively producing the cellular substance. For instance, an antibody directed to a membrane protein of interest can be used to rapidly label cells producing the membrane protein and the association of the antibody with the membrane protein producing cells can be rapidly detected by monitoring the change in the electrical properties of the cells before and after contact with the marker.

In another embodiment, the electrorotation chips described herein are used to analyze the electrical properties of particles (e.g., cells) that have been contacted with a test compound or agent. That is, methods of identifying an agent that modulates an electrical property of a cell are embodiments of the invention. The basic technical approach may be summarized as follows. When a test compound interacts with a cell, the interaction will trigger a series of biochemical reactions. These reactions will lead to a change in the electrical properties of the cell, which can be quickly monitored and analyzed using the methods described herein. On the other hand, if the agent does not interact with the cell, then the electrical properties of the cell would remain virtually unchanged, as if the cells were not exposed to such a compound. Thus, by analyzing the electrical properties of a plurality of cells before and after contact with an agent (e.g., compounds from a chemical or peptide library), many types of compounds can be rapidly screened for their ability to interact with the cell. As one of skill in the art will appreciate, in lieu of analyzing the cell before contact with the agent, cells that were contacted with the agent can be compared with a control population of cells that were not contacted with the agent. In this manner, agents that modulate an electrical property of a cell can be identified by virtue of their ability to alter the electrical property of a cell when contacted with the cell.

In other embodiments, methods to determine the identity or concentration of a molecule in a biological sample are provided. By one approach, an electrorotation chip that comprises a support with a plurality of EUs, as described above, is used to analyze the electrical properties of a molecule that has been contacted with particles that have been coated with a detection reagent (e.g., a dye, antibody or ligand that specifically binds to the molecule of interest). Accordingly, particles are coated with a detection reagent that binds to the particles so as to make coated particles and the coated particles are placed in a plurality of EUs, such that at least one coated particle is present in each EU. The coated particles are then contacted with a biological sample which may contain the molecule of interest and an electrical signal is applied to the EUs. Subsequently, the rotation of the coated particles is measured. The identity and/or concentration of the molecule of interest in the biological sample is determined by comparing the rotation of coated particles that were contacted with the biological sample with coated particles that were not contacted with the biological sample. As one of skill will appreciate, the identity and/or concentration of the molecule of interest in the biological sample can also be determined by comparing the rotation of coated particles that were contacted with the biological sample with control complexes of coated particles and molecules of interest. The section below describes the fabrication of the embodied electrorotation chips in greater detail.

Electrorotation Chip Embodiments

Several embodiments of the electrorotation chips use two layer electrode structures, having the advantages of simple electronic connection, simple fabrication processing, and high-throughput capabilities. Depending on the applications, different structures of the assay chambers are used. The chambers may contain multiple wells so that each well may correspond to one rotation field center. The chip substrate materials may be non-porous or porous (e.g. porous ceramics or porous silicon) solids so that the exchange of certain molecule types between the assay chambers and their environment (e.g., the penetration of $O_2$ and $CO_2$ molecules through the chip) is possible. Appropriate fluidic, electrical and mechanical controls are incorporated for the high throughput assay process. For monitoring and measuring rotation behaviors of particles, automatic optical detection and image processing coupled with microscopy may be used.

Embodiments also include microfabricated or micromachined electrorotation chips and the associated systems for high-throughput electrorotation assays. The electrorotation chip comprises many microelectrode elements that are arranged in such a way that several electrode elements form an electrorotation unit capable of producing rotating electric fields at the central region of the unit upon applying phase-shifted electrical signals to the elements. Multiple electrorotation units on an electrorotation chip are referred to as an "electrorotation unit array". Each electrorotation unit may be selectively addressable so that the rotating electric field generated at the unit can be turned on or off and can be modulated in terms of the field frequency, intensity and the direction of the field rotation. Alternatively, all or some of the electrorotation units may be energized in the same or similar way. The rotating electric fields produced on the chip's surface at multiple electrorotation units are used to induce rotations of particles of different types. Thus, the frequency-dependency of the particle rotation behavior is determined with appropriate measurement methods (e.g., cell automatic imaging and image processing to determine rotation rates) and is further analyzed to derive electrical properties of particles.

To produce a rotating electric field at each electrorotation unit, three or more electrode elements are used and are energized with electrical signals having different phases. One example of an electrorotation unit comprises four electrode elements uniformly and symmetrically positioned about the center of the electrorotation unit as shown in FIG. 1(D). When the electrode elements are energized with electrical signals having sequential phase offsets of 0, 90, 180 and 270 degrees, a rotating field is generated at the central region between the four elements.

Another example of an electrorotation unit comprises three identical electrode elements that are uniformly arranged about the center of the electrorotation unit as shown in FIG. 1(C). When these electrode elements are energized with electrical signals having sequential phase offsets of 0, 120 and 240 degrees, a rotational electrical field will be produced at the central regions between these electrode elements.

In general, the electrorotation units comprise of N identical electrode elements that are distributed about the center of the rotating electrical field. Preferably, the elements are uniformly and symmetrically spaced.

When electrical signals having phase offset values of 0, 360/N, 360*2/N, 360*3/N, . . . 360*(N−1)/N are connected to these electrode elements, a rotating electrical field is produced at the center of the unit. Here N is an integer and is larger than or equal to 3. Alternatively, the phase offset values of the electrical signals sequentially applied to the electrode elements may be 0, 360*k/N, 360*k*2/N, 360*k*3/N . . . and 360* k*(N−1)/N. Here N and k are both integers, N>=3, 1<=k<=N/2.

As an example, if N=4 and K=1, the electrorotation unit comprises of four electrode elements and the corresponding energizing electrical signals have phase offset values of 0, 90, 180 and 270 degrees (FIG. 1(D)).

The spatial electrical field distribution at the central regions between electrode elements depends on the specific values of N and k, the structure and dimensions of the electrode elements, and the amplitude and frequency of the applied electric signals.

The preferred embodiment comprises identical electrodes uniformly spaced about the central region and driven by signals of consistent phase offsets and amplitudes. As one skilled in the art will appreciate, other variations may also be utilized. For example, the dimensions and shape of the electrodes may not be identical, the distance of the electrodes to the center of the rotating electrical field may vary, or the spacing about the central region may not be symmetrical or uniform. These variations can be combined with variations in the amplitude and phase offset of the electrical signals to generate the desired rotating electrical field.

Those skilled in the theoretical analysis and numerical simulation of electromagnetic fields can analyze, simulate and optimize the rotating electrical field based on the values of N, k, the structure and dimensions of the electrode elements, and the amplitude and frequency of the applied electrical signals.

Electrode elements are made of three-dimensional, electrically conductive materials. They usually are thin films (less than several microns) that are deposited on substrates, although it is possible to fabricate an electrode element of greater thickness if needed. The footprint of an electrode element can be linear, concave or convex. Other geometrical shapes could also be used.

The electrode elements are electrical conductors having defined geometries fabricated or machined on the electrorotation chips. The conductors may be a metallic structure formed by deposition, evaporation, electroplating, or sputtering; or the conductors may be formed within a semiconductor layer through selective doping.

Depending on the application, the electrorotation chips may be fabricated on solid or porous substrate materials. The solid substrates include but are not limited to glass, silicon, plastics and ceramics. The porous substrates may be used in applications where the controlled exchange of certain molecules (e.g., gaseous molecules such as $O_2$ or $CO_2$) between the assay chambers and their surroundings is necessary.

Depending on the substrate materials and required electrode element structures, standard single- or multiple-layer photolithography may be used to produce the desired microelectrode elements on the electrorotation chips. Alternatively, other microfabrication or micromachining techniques may be employed. One example is thick-film printing of electrode structures on ceramics. Different fabrication techniques have their advantages and limitations with respect to the fabrication resolution and material choices. Those skilled in the art of microfabrication and micromachining could readily determine proper fabrication methods based on the microelectrode and electrorotation chip designs.

The electrorotation units may be arranged in a regular, repetitive pattern (e.g., a rectangular grid) or they may be arranged in an "irregular" or "random" pattern. An exemplary arrangement of an electrorotation unit array has a column and row structure of the form common in microelectronics. That is, the columns and rows are mutually perpendicular although the columns and rows can readily be offset at different angles (e.g., 80 degrees).

Preferably, the size of an electrorotation unit is between microns and several centimeters. That is, the length of the longest axis of an electrorotation unit can be less than 1 $\mu$m, less than 5 $\mu$m, less than 10 $\mu$m, less than 20 $\mu$m, less than 50 $\mu$m, less than 75 $\mu$m, less than 100 $\mu$m, less than 150 $\mu$m, less than 200 $\mu$m, and less than 250 $\mu$m, less than 500 $\mu$m, less than 750 $\mu$m, less than 1 mm, less than 2 mm, less than 3 mm, less than 4 mm, less than 5 mm, less than 6 mm, less than 7 mm, and less than 8 mm, less than 9 mm, less than 10 mm, less than 15 mm, less than 20 mm, less than 30 mm and less than 50 mm. Typically, the electrorotation unit comprises three or more electrode elements arranged about a center region where a rotating field can be produced.

Individual electrorotation units may be selectively addressable so that at any instant there may be only a single energized electrorotation unit generating a local rotating field or there may be multiple energized units each of which generates a rotating field. The addressing of electrorotation units refers to applying appropriate electrical signals to the electrode elements in an electrorotation unit.

Depending on the electrorotation chip configuration, selective addressing of electrorotation units can be realized through different mechanisms. In one configuration, every element in each unit is connected to a separate external electrical signal source so that each unit can be selectively addressable.

Alternatively, electronic switches could be used to address the individual units. Whether an electrode element is electrically energized would then be determined by the on/off status of the electronic switch for the element. Additional electronic signals are needed for controlling these switches. Selective electronic addressing is commonly used in modern microelectronics, for example, in electronic memory chips. Those skilled in microelectronics could readily adopt the selective addressing methods for the electrorotation chips described here.

The phase-shift caused by the use of switches should be considered when determining the layout and grouping of the electrorotation units. One embodiment uses similar switches for all of the signal sources, so that the phase shift of each signal is equivalent. Alternatively, a resistor-capacitor network may be used in an analogue circuit to compensate for the phase shift. A third alternative is to adjust the phase of the signal generators. Those skilled in electronics could design and implement appropriate circuits according to the specific signals required.

Figure 5:
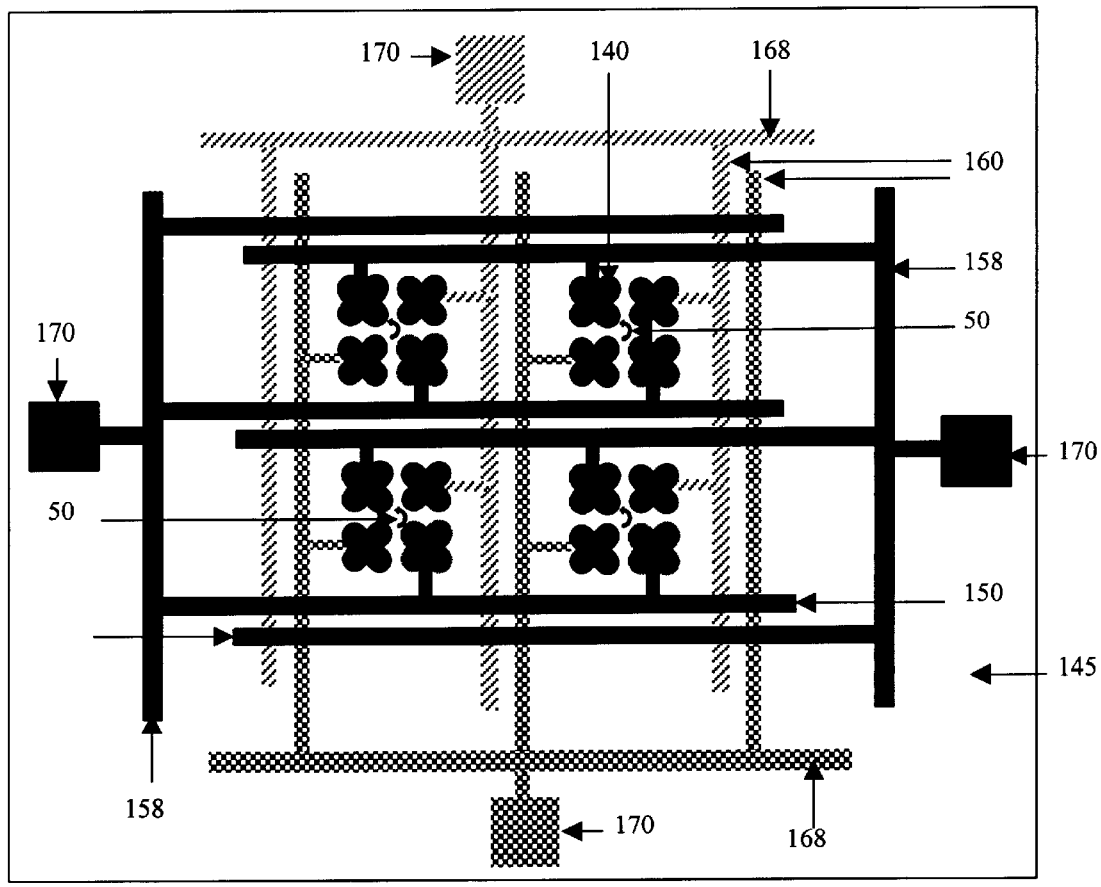
FIG. 5 shows a schematic drawing of one embodiment for a high-throughput electrorotation chip. Four electrode elements each having a butterfly footprint form one electrorotation unit.

In another chip configuration, all the electrorotation units are connected in parallel to the signal sources and are energized or disconnected simultaneously (See e.g., FIG. 5). In yet another configuration, the electrorotation units are divided into a number of groups where the electrorotation units within each group are connected in parallel to the signal sources. In this case, the units within the same group may be energized or disconnected simultaneously.

Embodiments can also have assay chamber structures of various shapes and sizes. The assay chambers refer to the three dimensional spaces where rotating electrical fields are generated and particles to be assayed are placed. In a simple chamber configuration, an assay chamber consists of an electrorotation chip on the bottom, and a plate that has a hole in the middle which is bound together with the electrorotation chip. The hole in the plate may be of any shape but should be open at the positions corresponding to the electrorotation centers on the chip.

Figure 2:
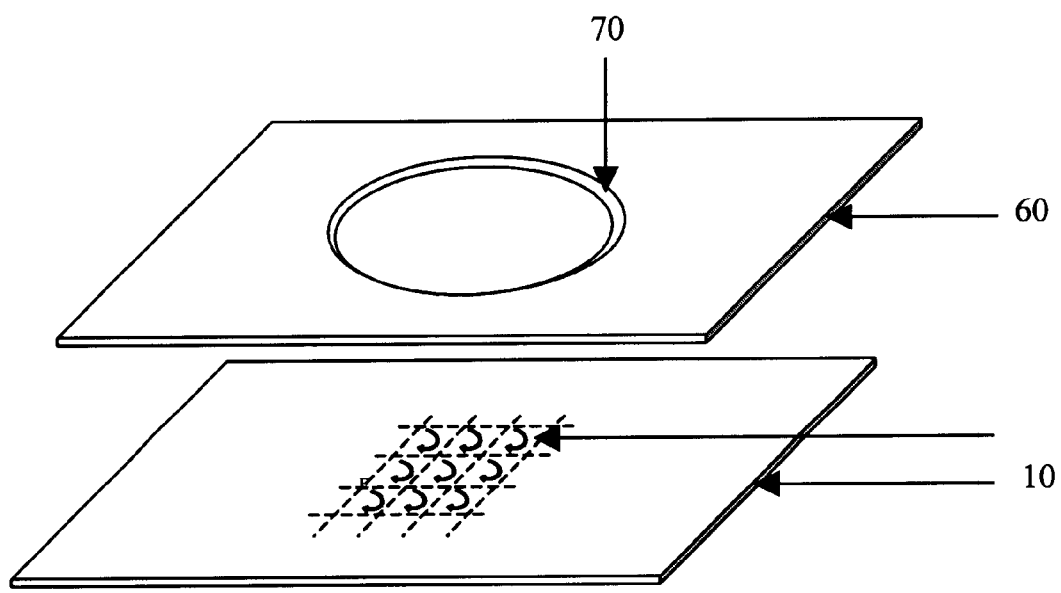
FIG. 2 shows a plate with a single hole for a plurality of electrorotation units.

FIG. 2 shows a hole over all the electrorotation units on the chip. When the plate is bound with the chip, the hole space corresponds to a well in the chamber. Particles to be assayed (e.g., a small volume of aqueous solutions consisting of different types of particles) are introduced into the well. Such single-well chambers may be used for the assays in which many types of particles are mixed together and are introduced for electrorotation assay simultaneously.

Figure 3:
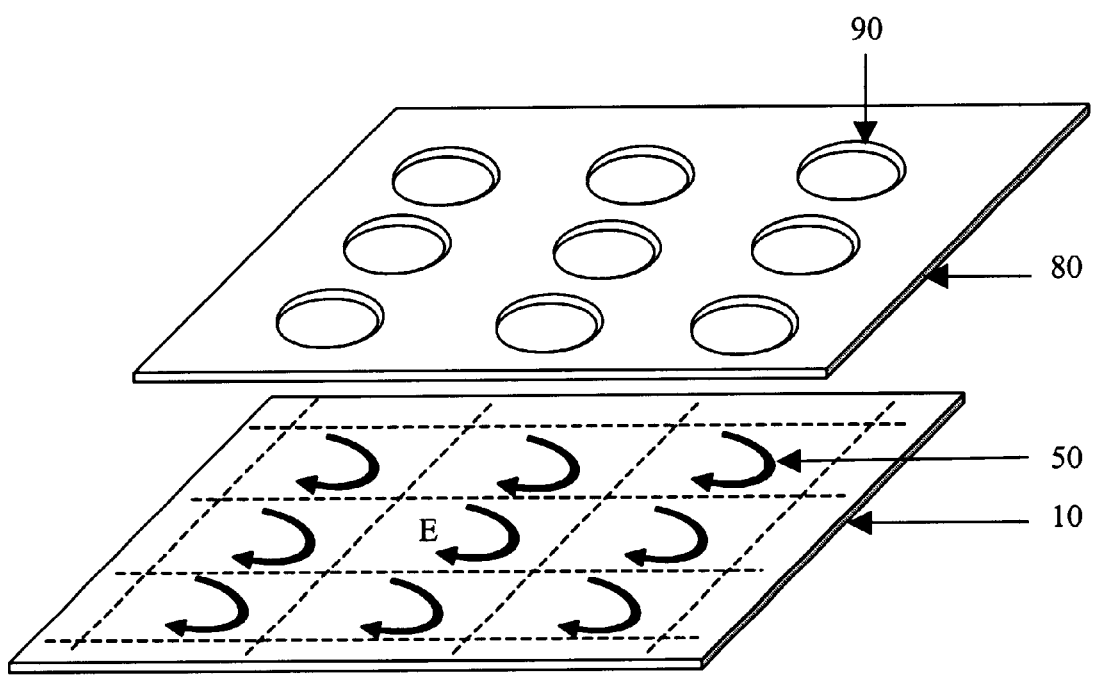
FIG. 3 shows a plate with a plurality of holes wherein each hole provides access to one electrorotation unit.

FIG. 3 shows another chamber configuration, with many holes on the plate. Each hole is located at a position corresponding to the central region of one electrorotation unit on the chip. There are the same numbers of electrorotation units on the chip as there are holes on the plate. When the plate is bound to an electrorotation chip in such a way that the holes and electrorotation unit centers are aligned, each hole forms a reaction well in the assay chamber.

The plate for constructing the assay chamber may be made of different materials such as glass, silicon, ceramics, Teflon sheets or other plastic thin film sheets, polymer materials such as PDMS (Poly-dimethylailoxane) and PMMA (polymethylmetacrylate), PC (polycarbonate).

For example, glass plates may be used and holes of appropriate sizes may be drilled or etched with photolithography, depending on the dimension of the holes and the glass thickness. In general, the characteristic size of the holes is in the range between tens of microns and several centimeters. The glass plates may be bound to electrorotation chips made of silicon substrate through anodic bonding. Another example is to use thin-film sheets of thickness in the range between tens of microns and several millimeters. The holes of different shapes may be cut or micromachined on the sheets.

Still another example is to use polymer materials as the plates to bind with electrorotation chips and to form assay chambers. Polymer materials may be processed to produce required holes.

The following fabrication methods may be used, including laser ablation (e.g.: Simpson PC, Roach D, Woolley A T, Thorsen T, Johnston R, Sensabaugh G F, Mathies R A, *Proc. Natl. Acad. Sci., USA*, 95: 2256–2261, 1998), herein expressly incorporated by reference in its entirety; injection molding (e.g.: Integrated capillary electrophoresis for chemical analysis by Becker H and Manz A, in: Sensors Update, Vol. 3, editors: Baltes H, Gopel W and Hesse J. VCH Weinheim, pp 208–238, 1998), herein expressly incorporated by reference in its entirety; silicon rubber casting (e.g.: Manz A and Becker H, editors, Microsystem technology in Chemistry and Life Science, Topics in Current Chemistry, 194, Spring Heidelberg, 1998), herein expressly incorporated by reference in its entirety; embossing (e.g.: Kopp MU, Crabtree HJ and Manz A, Current opinion in Chem. Biol., 1:410–419, 1997), herein expressly incorporated by reference in its entirety; molding (e.g.: Microfluidic networks for chemical patterning of substrates: design and application to bioassays by Delamarche E, Bernard A, Schmid H, Bietsch A, Michel B and Biebuyck H, *J. Am. Chem. Soc.*, 120: 500–508, 1998, herein expressly incorporated by reference in its entirety; and Integrated capillary electrophoresis on flexible silicone microdevices: analysis of DNA restriction fragments and detection of single DNA molecules on microchips by Effenhauser C S, Bruin G J M, Paulus A and Ehrt M, Anal. Chem., 69: 3451:3457, 1997), herein expressly incorporated by reference in its entirety. The section below describes the operation of the embodied electrorotation chips in greater detail.

Operation of the Electrorotation Chips

During the electrorotation assay, the assay chamber may be open. Particle suspensions or solutions are introduced into the chamber wells, and particles' electrorotation behaviors are then determined with the chamber well open.

Alternatively, after introducing particle suspension, a cover plate may be used to seal the chamber well, thus forming an enclosed chamber. Desirably, the cover plates are optically transparent so that the determination and measurement of particle electrorotation responses may be achieved by monitoring particle rotation through the cover plate. Alternatively, the chamber wells are pre-sealed, and the particle suspension is introduced through fluidic channels on the electrorotation chip or on the cover plates. When multiple assay wells are used with this configuration, appropriate microfluidic circuits are designed for the fluidic flow and control necessary for loading particle suspensions into different reaction wells.

The phase-sequential electrical signals necessary for driving the electrode elements to produce a rotating electrical field are generated from signal generators. The signal generators could be located on the electrorotation chip or connected electrically to the electrorotation chip from another source. The signals could be a sinusoidal waveform, square waveform or other periodic waveform. Although sinusoidal waveforms are preferred, other waveforms may be used. There are a number of methods to design and construct such signal generators. In one approach, a phase-shifting resistor-capacitor network may be used in an analogue, oscillation circuit to produce phase-sequential signals. Alternatively, digital circuits with proper clock control may be used to build phase-sequential signals. Those skilled in electronics could design and implement appropriate electronic circuits according to the specific electronic signals required.

The frequencies of the electronic signals generally lie in the range between several Hz and several hundred MHz. Depending on the particle types to be assayed, frequencies out of this range may also be appropriate. Specific applications may use a narrow frequency band for the electrorotation assay. For example, the assay of typical mammalian cell properties such as cell membrane composition or structure may employ signals in the frequency range between 10 kHz and 10 MHz.

To produce sufficiently strong rotating electrical fields, the amplitudes of the electronic signals may be in the range between 100 mV (RMS) and 20 V RMS. Because the rotating field strength also varies with the dimensions of the electrorotation units, the amplitudes of the electronic signals are not limited to this range. For example, electrorotation units smaller than 10 microns or greater than several mm may require a signal amplitude greater or smaller than this range.

Particle electrorotation behaviors may be determined or measured using different approaches. Typically, microscopy with various magnification factors (between 10 and 10000) is needed for observing the particle rotation.

Manual determination of particle rotation rate is possible although it is lab intensive and time-consuming. For high-throughput assay applications, automatic imaging system are desired so as to facilitate the rapid measurement of the rotational responses of the particles.

In one embodiment, the imaging system comprises an optical microscope, imaging camera, image grabber (the device for recording images of particle rotation into digital data file format), and image processor and analyzer. Various modern signal-processing methods and image-processing techniques may be used to achieve the desired resolution and accurate rotation rate measurements. Those skilled in image processing and signal processing may determine the specific approaches and produce the analysis software for calculating cell rotation rate based on electronic imaging data. One such imaging system for automatic measurement of cell electrorotation has been developed and reported by Giovanni et al. (Automatic electrorotation: dielectric characterization of living cells by real-time motion estimation. De Gasperis et al., *Meas. Sci. Technol.* 9: 518–529, 1998), herein expressly incorporated by reference in its entirety.

Many electrorotation theories can be applied to derive the electrical parameters for each particle whose electrorotation behavior is measured. The followings are provided as reference to the many applications of electrorotation theory that can be adapted for use with an embodiment described herein. (See e.g., Fuhr et al., *Stud. Biophys.* 108: 149–164 (1985), herein expressly incorporated by reference in its entirety; Gimsa et al., *Physical characterization of biological cells*, Schutt W, Klinkmann H and Laprecht I and Wilson T editors, Gesundheit, Berlin, pp 295–323, 1991, herein expressly incorporated by reference in its entirety; Huang Y et al., *Phys. Med. Biol.*, 37: 1499–1517 (1992), herein expressly incorporated by reference in its entirety; Wang et al., *Biochim. Biophys. Acta*. 1193: 185–194 (1994), herein expressly incorporated by reference in its entirety; Gascoyne et al., *Bioelectrochem. Bioenerg.* 36:115–125 (1998), herein expressly incorporated by reference in its entirety; and Yang et al., *Biophys. J.*, 76: 3307–3314 (1999), herein expressly incorporated by reference in its entirety). Some of the mathematical formulae and electrorotation theories that can be used to interpret the results generated by the embodiments described herein are also provided in Example 1. The section below describes several of the biological applications that can be performed using an electrorotation chip fabricated as described herein.

Biological Application for the Electrorotation Chip Embodiments

Embodiments of the invention include methods for high-throughput analysis of the electrorotation properties of a variety of biological particles and complexes. Accordingly, the electrical properties of a plurality of particles (e.g., cells that may or may not be attached with an antibody, ligand, or other molecule) can be rapidly determined using the electrorotation chip described herein. By one approach, a plurality of particles are added to the EUs on an electrorotation chip, prepared as described above, such that at least one particle is present in each EU. Next, a rotating electrical field is applied to the EUs so as to induce the particles to rotate. Although the rotational behavior of the particles can be measured at one frequency, desirably, the rotational behaviors of the particles are measured at multiple frequencies over a particular frequency range. Because the electrorotation chips of the invention comprise a plurality of EUs that can be independently addressable, a high-throughput analysis of many particles with varying properties is provided.

Many different types of particles and biological events can be analyzed by the embodiments described herein. For example, the electrical properties of particles, including but not limited to, biological molecules, biological complexes, immune complexes, liposomes, protoplasts, platelets, virus, and cells can be determined using an embodiment described herein. Preferably, the size (e.g., the length of the longest axis of the particle) of the particles analyzed by an embodiment range from about 0.05 $\mu$m to approximately 100 $\mu$m. That is, the length of the longest axis of the particle can be less than or equal to 0.1 $\mu$m, 1 $\mu$m, 5 $\mu$m, 7 $\mu$m, 10 $\mu$m, 12 $\mu$m, 15 $\mu$m, 20 $\mu$m, 25 $\mu$m, 35 $\mu$m, 40 $\mu$m, 45 $\mu$m, 50 $\mu$m, 55 $\mu$m, 60 $\mu$m, 65 $\mu$m, 70 $\mu$m, 75 $\mu$m, 80 $\mu$m, 85 $\mu$m, 90 $\mu$m, 100 $\mu$m, 200 $\mu$m and 300 $\mu$m.

Depending on the specific electrorotation assay application, particles to be assayed are placed or suspended into aqueous or non-aqueous solutions, or are used directly in air or vacuum. The particle-suspending solutions are chosen properly in terms of their electrical properties (electrical conductivity and dielectric permittivity) so as to maximize the difference in electrical properties between the particles and their suspending solutions and to obtain largest electrorotation responses. If viable cells are being analyzed, the suspension solutions should be optimized so as to maintain viability, and if needed, the normal growth of the cells. Maintaining cell growth can involve not only a special growth medium but may also require gaseous molecules to be dissolved in the medium. To accommodate these applications, the electrorotation chip support can be fabricated from gas-permeable materials such as porous ceramics or porous silicon (silicon may be selectively etched to some extent), which allow the exchange of the gaseous molecules between the medium in the assay chambers and their surroundings.

In some embodiments, the electrical properties of the particles are analyzed by taling electrorotation measurements directly on the particles themselves, while in other embodiments, the electrical properties of the particles are analyzed indirectly by monitoring the electrorotational behavior of microbeads that have been attached to the particle of interest. In some cases, in particular when small particles are under analysis, it is advantageous to use an indirect approach so as to increase the sensitivity of the assay. Generally, the indirect approach involves using a marker, such as a dye, antibody, bead, carrier, or other ligand, which is more easily analyzed than the particle itself. In some cases, electrorotation measurements are made on the marker themselves and in others the marker, when associated with the particle, perturbs the electrical properties of the particle such that analysis of the particle itself is facilitated.

One indirect approach, for example, involves the use of an antibody coated bead. To make the antibody coated beads, beads or a resin (e.g., polystyrene microparticles of 6 $\mu$m diameter approximately 1×10$^8$ beads/500 $\mu$l) are resuspended in a suitable buffer (e.g., phosphate buffered saline) and are contacted with an equal volume of antibody solution (e.g., approximately 100 $\mu$g/ml). The beads and antibody solution are placed on a rocker at 4° C. and are rocked over night. Subsequently, 500 $\mu$l of a blocking protein (e.g., 1.0% BSA) and 500 $\mu$l of a blocking RNA (e.g., tRNA), which are used to block the sites of non specific binding on the beads, are added. The blocking reaction is also carried out at 4° C. for approximately 2 hours. The resulting antibody coated beads have a large quantity of antibody bound to the bead and these beads can be used to interact with a particle.

Next, the antibody coated beads are contacted with a particle that is antigenic to the antibody and the bead/antibody/particle complexes are provided to the EUs on an embodiment of the electrorotation chip described herein. An electrical signal is applied and electrorotation measurements are taken on beads that were complexed with the particle. As a control, electrorotation measurements on antibody-coated beads that were not contacted with a particle are made. Preferably, electrorotation measurements are made on the same beads before contact with the particle. By comparing the values obtained from the electrorotation measurements of the beads before and after contact with the particle, one of skill can indirectly detennine the electrical properties of very small particles including peptides and nucleic acids. (See e.g., WO 93/16383, herein expressly incorporated by reference in its entirety, for more discussion of indirect approaches to evaluate the electrical properties of a particle in a single EU electrorotation system.)

Advantageously, some embodiments are capable of measuring the electrical properties of a plurality of particles of various types, shapes, and sizes. (See Examples 8 and 9). Most typically, for example, a biological sample contains a heterogeneous population of particles. The embodiments described herein can be used to identify homogeneous populations of particles within a heterogeneous biological sample by classifying and grouping the various particles according to their electrical properties. Accordingly, aliquots of a biological sample are placed in individual EUs and electrorotation measurements are taken on the individual particles within each EU. The data is compiled and particles having similar electrical properties are classified and grouped. That is, particles that have similar electrical properties are identified.

For some applications, for example, the ability to differentiate cells that produce a cellular substance from those that do not is desired. Cells that are actively producing a cellular substance (e.g., carbohydrate, lipid, or peptide) exhibit different electrical properties than cells that are not actively producing a cellular substance. An embodiment described herein can be used to rapidly screen a plurality of cells for their ability to produce a cellular substance. For example, cells can be transfected (e.g., at a low efficiency) to express a membrane protein, such as epidermal growth factor receptor (EGF receptor). Some population of the cells that underwent transfection will not express the membrane protein and some population will express the membrane protein. Thus, after transfection, a heterogeneous population of cells are obtained. The techniques described above can then be employed to identify a homogeneous population of cells within the heterogeneous population of transfectants.

Accordingly, antibodies to the EGF receptor are generated or are obtained from a commercial supplier (Sigma). These antibodies are then attached to beads using the technique described above or by forming a covalent linkage through a hydroxy, carboxy or amino group and a reactive group on the carrier. Many kits for immobilizing antibodies to beads are commercially available (Pierce Chemical). The immobilized antibodies are then used to react with the heterogeneous population of cells. The cell/antibody/bead mixture is applied to a plurality of EUs on an embodiment of an electrorotation chip and an electrical signal is provided. Electrorotation measurements are taken on the beads before and after contact with the cells. The electrical properties of the beads that successfully bound to an EGF receptor expressing cell will be different than the electrical properties of the beads themselves. In this manner, a homogeneous population of cells that are producing a cellular substance are identified. Of course, electrorotation measurements can be made directly on the membrane protein expressing cells and, in some cases, largely dependent on the protein expressed, differences in the electrical properties of cells actively producing the substance from cells not producing the substance can be measured. For example, cells that express proteins involved in ion transport would have electrical properties that are significantly different than cells that do not express these transport proteins and can be directly analyzed using an embodiment of the invention.

In addition to analyzing the electrical properties of various particles, embodiments described herein can be used to detect whether a reaction or interaction has occurred between a cell and a molecule (e.g., antibody, peptide, chemical, or other cell). By one approach, for example, the electrorotation behavior of a cell or plurality of cells prior to exposure to a molecule of interest (referred to as a "binding partner" by virtue of the determined association with a particle or referred to as a "candidate binding partner" by virtue of the lack of certainty as to whether the molecule will associate with the particle) is determined. Preferably, various electrical properties are analyzed for these "control sample(s)". Next, a cell or plurality of cells is contacted with the binding partner, a sufficient time for interaction is provided, and the electrorotation behaviors of the exposed cell or plurality of cells are analyzed with an embodiment described herein. Preferably, the identical parameters that were used to analyze the control sample(s) are used to analyze the exposed cell or plurality of cells. A comparative analysis can then be made between the control sample(s) and the exposed cell or plurality of cells and, from this information, the effect of the binding partner on the cell or plurality of cells can be determined. As described above, indirect measurement approaches can be used, as well.

Preferably, the electrorotation behaviors of individual cells prior to the exposure to the binding partner are measured and statistically analyzed. The statistical analysis may be a simple average of the measured rotation rate for individual cells at various frequencies. Accordingly, the individual cells are incubated with a candidate binding partner, the electrorotation behaviors are measured, and a statistical analysis is performed. The statistical data for the cells before and after incubation with the various candidate binding partners are then compared to see whether a significant change in cell electrorotation properties has occurred.

By one approach, for example, a high-throughput electrorotation assay can be used to screen a chemical compound library for binding partners that modulate the electrical properties of cells. (See Example 10). Accordingly, cells suspended in an appropriate media are introduced into multiple reaction wells in an electrorotation assay chip. Each well is equilibrated such that an approximately similar number (e.g., between 10 and 500) cells are present. Chemical compounds ("candidate binding partners") from a compound library are added to these wells such that one compound/well is accommodated. If the added compound is dissolved in a solvent, a small but concentrated aliquot of the compound solution is used. The cells are then incubated with the compounds for a sufficient time to allow for an interaction. Preferably, the electrorotation behaviors of the cells are determined before and after the incubation of cells with the chemical compounds, however, control cells that were not contacted with the chemical can be used in the alternative. The electrorotation behavior for cells in each well is measured and population parameters are derived so as to determine whether a significant change in the parameters occurred following the incubation of the cells with the compounds. For example, if a chemical interacts with the cells, it will cause a biochemical reaction that will alter the biological properties of the cells, which will be detectable as a statistically significant change in an electrical property. Such changes in cell electrical properties can be detected by electrorotation measurements and the compounds that cause such changes can be identified as lead drug molecules. On the other hand, if a chemical compound does not interact with the cells, the cells will not exhibit a change in their electrorotation behavior.

In a simple case, the electrorotation behavior of the cells at a single characteristic frequency is measured. As the name implies, the "characteristic frequency" is a frequency at which the electrorotation behavior of the cells strongly depends on the cell properties. The characteristic frequency can also be the frequency at which the cells, prior to exposure to the candidate binding partner, exhibit no or very little rotation. Thus, if the cells, after the incubation with a candidate binding partner, exhibit a strong no-zero rotation at this frequency, one can conclude that the cells have interacted with the binding partner. That is, if the interaction between the cells and the candidate binding partner has caused a change in cell electrorotation behaviors then one can conclude that the candidate binding partner is indeed a binding partner. On the other hand, if the average of rotation rates for individual cells after incubation with a candidate binding partner is also close to zero at this frequency, one may conclude that there is no change in cell electrorotation properties and the candidate binding partner does not interact with the cell.

Another method for determining whether the cells exhibit a statistically-significant change in cell properties before and after incubation with different types of assay molecules is to compare cell dielectric parameters. Accordingly, the measured electrorotation responses of individual cells are analyzed by performing mathematical fitting for the experimental rotation rates over the measured frequency range with a theoretical curve. The theoretical dependency of cell rotation rate on the frequency of the applied field is calculated using cell models and dielectric parameters in the model. The theoretical curves follow certain mathematical formulas (e.g. written analytical formula or the numerical relationships) with one or multiple parameters that may be varied to adjust the curve shapes. Thus, the fitting procedure may lead to one or multiple parameters in the model for each measured cell (See e.g., Example 1, equation (7)). These derived parameters can then be analyzed further using statistical methods to obtain population parameters and to compare these population parameters to determine whether statistically-significant changes occurred after the cells are incubated with a candidate binding partner.

Another group of embodiments concern the quantitative analysis of the interaction between a plurality of cells and a binding partner (e.g., chemical, peptide, antibody, or other ligand). In some applications, for example, embodiments of the invention can be used to determine the identity or concentration of a molecule in a biological sample. In other applications, it may be desired to determine the optimum concentration of a molecule that should be applied to cells. In this later application, the optimum concentration of a molecule to be added to a cell can be determined by evaluating the amount of binding partner needed to achieve a maximum electrorotation response.

These assays can be performed by using the approaches described above with slight modification. For example, the optimal amount of a compound to add a cell can be determined as follows. Various concentrations of binding partners are added to the cells in different reaction wells in a high-throughput electrorotation assay chamber, prepared as described herein. That is, a titration of binding partner is run on the electrorotation assay chamber such that different concentrations of the binding partner are present at each EU. After a sufficient time for incubation is allowed, the electrorotation behaviors of the cells in the different reaction wells are measured and the concentration of binding partner that leads to a maximum response is identified.

To determine the identity and concentration of a molecule in a biological sample, an indirect electrorotation analysis is used. (See Example 11). This method can employ surface-activated microparticles, to which a detection agent is bound. The detection agent on microparticle surfaces (e.g., a dye, antigen, antibody, peptide, enzyme, nucleic acid, or other ligand) interacts with a molecule of interest in a biological sample. Multiple detection reagents that bind specifically to different microparticles and interact specifically with different target molecules can be used so that more than one target can be evaluated in the same assay.

Accordingly, the surface-coated microparticles are introduced into multiple reaction wells in the assay chamber. The electrorotation behaviors of the microparticles are determined before contact with the biological sample. The biological sample is then added to each reaction well and a sufficient time for interaction is provided. After incubation, the electrorotation behaviors of the microparticles are measured. The measured values are then evaluated to determine whether a change in electrorotation behavior has occurred and to determine the magnitude of such change. The change in the cell rotation response will determine whether the biological sample contains molecules that interact with the coated microparticles. Furthermore, the change in the electrorotation response will correlate directly with the concentration of such molecules in the solution. By analyzing the changes in the electrorotation behaviors of the coated microparticles the composition and concentration of the molecule in the biological sample can be determined. The example below describes several electrorotation theories and their application to the embodiments described herein.

EXAMPLE 1

The following describes several electrorotation theories and their application to discern small changes in electrorotation properties of particles. A rotating electric field in the x-y plane of a Cartesian coordinate system may be described as:

$$\vec{E} = E_x \cos(\omega t)\vec{a}_x + E_y \sin(\omega t)\vec{a}_y \tag{1}$$

where $$\vec{a}_x \text{ and } \vec{a}_y$$

are the unit vectors along x-direction and y-direction, respectively, and $E_x$ and $E_y$ are the magnitude of the field along x- and y-directions. For an ideal rotating electric field, the field components satisfy the following equality: $E_x = E_y$. The rotating torque exerted on particles suspended in a medium can then be given by:

$$\vec{\Pi} = -4\pi r^3 \varepsilon_m \text{Im}(f_{CM}) E_x E_y \vec{a}_x \times \vec{a}_y \tag{2}$$

where $\varepsilon_m$ is the dielectric permittivity of the medium, r is the particle radius, and $\text{IM}(f_{CM})$ is the imaginary component of the dielectric polarization factor $f_{CM}$ of the particle. The polarization factor $f_{CM}$ can be given by:

$$f_{CM} = \frac{(\varepsilon_p^* - \varepsilon_m^*)}{(\varepsilon_p^* + 2\varepsilon_m^*)} \tag{3}$$

where $\varepsilon_p^*$ and $\varepsilon_m^*$ are the complex dielectric permittivities of the particle and medium, respectively. The complex dielectric permittivity is related to the frequency f of the applied field, electrical conductivity σ and dielectric permittivity $\varepsilon$ and can be defined as:

$$\varepsilon^* = \varepsilon - j\sigma/(2\pi f) \tag{4}$$

where the conductivity and permittivity may be frequency dependent parameters. Different particles may have different frequency-dependent electric conductivity and permittivity. In a typical electrorotation analysis, for example, the particles are suspended in a liquid (e.g., biological cells or polystyrene beads in an aqueous solution), the equilibrium particle rotation rate $R_{rot}$ under the balance between the torque (as given by equation 2), and viscous drag can be given by:

$$R_{rot} = -\frac{\varepsilon_m \text{Im}(f_{CM}) E_x E_y}{2\eta} \tag{5}$$

where η is the dynamic viscosity of the medium. Thus, the particle electrorotation rate $R_{rot}$ can depend on the particle dielectric polarization factor $f_{CM}$.

The measurements described above also allows for the determination of particle dielectric properties (e.g., electrical conductivity and dielectric permittivity). Depending on the structure and composition of the particle to be analyzed, preferably, the electrical properties of the particles are analyzed with various dielectric models. For example, a plurality of cells are simulated with shelled spheres. For a single-shell model, the shell and its inner sphere correspond to the cell membrane and cell interior, respectively. Complex dielectric permittivity of the shelled spheres can be given by:

$$\varepsilon_{cell}^* = \varepsilon_{mem}^* \frac{\left(\frac{r}{r-d}\right)^3 + 2\varepsilon_{int}^* - \frac{\varepsilon_{mem}^*}{\varepsilon_{int}^* + 2\varepsilon_{mem}^*}}{\left(\frac{r}{r-d}\right)^3 - \frac{\varepsilon_{int}^* - \varepsilon_{mem}^*}{\varepsilon_{int}^* + 2\varepsilon_{mem}^*}} \tag{6}$$

where $\varepsilon_{cell}^*$, $\varepsilon_{mem}^*$ and $\varepsilon_{int}^*$ are complex dielectric permittivity of the cell, the membrane, and the cell interior, respectively. The parameters r and d represent the cell radius and membrane thickness, respectively.

When electrorotation is applied to analyze cells, cell dielectric parameters ($\in_{mem}^*$ and $\in_{int}^*$) can be determined from the frequency dependency of cell rotation rate. Typically, this is accomplished through a simulation that fits the theoretical ($R_{rot\_theory}(f_i)$) electrorotation spectra to the experimental ($R_{rot\_exp}(f_i)$) data by adjusting the cell dielectric parameters:

$$\min_{parameters} |(R_{rot\_exp}(f_i) - R_{rot\_theory}(f_i))| \qquad (7)$$

where $f_i$ refers to the experimental frequency points. A number of papers in the literature described the methods to analyze electrorotation spectra and to derive cell dielectric parameters. We provide here following reference papers as examples, Interpretation of electrorotation of protoplasts I: the theoretical consideration by Fuhr G, Gimsa J, Glaser R, *Stud. Biophys.* 108: 149–164, 1985, herein expressly incorporated by reference in its entirety; Theory and application of the rotation of biological cells in rotating electric field by Gimsa J, Glaser R and Fuhr G in *Physical characterization of biological cells*, Schutt W, Klinkmann H and Laprecht I and Wilson T editors, Gesundheit, Berlin, pp 295–323, 1991, herein expressly incorporated by reference in its entirety; Differences in the AC electrodynamics of viable and non-viable yeast cells determined through combined dielectrophoresis and ROT studies by Huang Y, Holzel R, Pethig R and Wang X-B *Phys. Med. Biol.*, 37: 1499–1517, 1992, herein expressly incorporated by reference in its entirety; Changes in friend murine erythroleukaemia cell membranes during induced differentiation determined by ROT by Wang X-B, Huang Y, Gascoyne PRC, Holzel R, and Pethig R, *Biochim. Biophys. Acta.* 1193: 185–194, 1994, herein expressly incorporated by reference in its entirety; Numerical analysis of the influence of experimental conditions on the accuracy of dielectric parameters derived from ROT measurements by Gascoyne PRC, Becker FF and Wang X-B, *Bioelectrochem. Bioenerg.* 36:115–125, 1998, herein expressly incorporated by reference in its entirety; Dielectric properties of human leukocyte subpopulations determined by electrorotation as a cell separation criterion by Yang J, Huang Y, Wang X, Wang X-B, Becker FF and Gascoyne PRC, *Biophys. J.*, 76: 3307–3314, 1999, herein expressly incorporated by reference in its entirety.

After dielectric parameters of individual measured particles are derived, the parameters may then be further analyzed using statistical methods to obtain population parameters (e.g., means and standard deviations of certain parameters) for each particle type. These population parameters may then be used for further analysis such as comparing the differences between populations.

The electrorotation theories explained above are applicable to various electrorotation layouts. The following example shows various embodiments of electrorotation units.

EXAMPLE 2

FIG. 1(A) shows a schematic outline for a high-throughput electrorotation chip 10. The chip comprises multiple electrorotation units 20, and each electrorotation unit 20 comprises multiple electrode elements 30. When appropriate electrical signals 40 are applied, the electrorotation unit 20 generates a rotating electrical field 50 that lies in the plane parallel to the electrorotation chips 10 and rotates along the axis normal to the chip.

FIG. 1(B) shows an electrorotation unit comprising three narrow-width rectangular electrode elements 30 that are uniformly distributed about the center of the electrorotation unit. When electrical signals having phase values of 0, 120 and 240 degrees are applied to these electrode elements, a rotating electric field may be formed at the central region between these elements.

FIG. 1(C) shows an electrorotation unit comprising six narrow-width rectangular electrode elements 30 that are uniformly distributed about the center of the electrorotation unit. When electrical signals having phase values of 0, 60, 120, 180, 240 and 300 degrees are applied to these electrode elements, a rotating electric field may be formed at the central region between these elements.

FIG. 1(D) shows an electrorotation unit comprising four narrow-width rectangular electrode elements 30 that are uniformly distributed about the center of the electrorotation unit. When electrical signals having phase values of 0, 90, 180 and 270 degrees are applied to these electrode elements, a rotating electric field may be formed at the central region between these elements.

The chips may be fabricated on non-porous materials (e.g., glass, silicon, ceramics, plastics) or porous (e.g., porous silicon, porous ceramics) materials and are rectangular, round, or other shapes. The porous chip material may be used to allow various types of gaseous molecules to penetrate through the chip material. The size of the chip may vary between 1 mm and 500 mm. The size of the electrorotation unit may vary between 10 microns and 10 mm, depending on the size and shape of particles under electrorotation assay.

The chips typically comprise at least one assay chamber, as illustrated by the following example.

EXAMPLE 3

FIG. 2 shows a schematic representation of one embodiment for a high-throughput electrorotation chamber. The chamber consists of an electrorotation chip 10 and a plate 60 bound together. For the sake of clarity in the presentation, the chip 10 and the plate 60 are shown separately in FIG. 2. There is only one hole 70 cut in the plate 60 so that when the plate 60 is bound together with the chip the hole covers all the electrorotation units in the chip to form an assay well. Particles to be assayed are introduced into the well and are analyzed at different rotation field centers.

EXAMPLE 4

FIG. 3 shows a schematic representation of another embodiment for a high-throughput electrorotation chamber. The chamber consists of an electrorotation chip 10 and a plate 80 bound together. For the sake of clarity in the presentation, the chip 10 and the plate 80 are shown separately in FIG. 3. There are multiple holes 90 cut in the plate 80 so that when the plate 80 is bound together with the chip each hole covers one electrorotation unit in the chip to form an assay well. Particles of different types are introduced into these wells so that each particle type occupies one and only one assay well. They are analyzed in the rotation fields.

The plates for constructing the assay chamber may be made of various types of materials, including glass, silicon, ceramics, Teflon sheets or other plastic thin film sheets, polymer materials such as PDMS (poly-dimethylailoxane) and PMMA (polymethylmetacrylate), PC (polycarbonate). Depending on the application, porous or non-porous materials, as well as rigid or elastic materials may be used.

Glass is an example of a material that may be used. Holes of appropriate sizes may be drilled or etched with photolithography on the glass plate, depending on the dimension of the holes and the glass thickness. Typically, the characteristic size of the holes is in the range between tens of microns and several centimeters. The glass plates may be bound to electrorotation chips made of silicon substrate through anodic bonding. Another example is to use thin film Teflon sheets of thickness in the range between tens of microns and several millimeters. The holes of different shapes may be cut or micromachined on the sheets. Polymer materials may be processed to produce required holes and used to bind with electrorotation chips and to form assay chambers.

The plates made of polymer materials may be bound to electrorotation chips using different methods, depending on the specific materials of the polymer and the chip. For example, a plate made of PDMS (poly-dimethylailoxane) may be bound to silicon electrorotation chip to form a sealed chamber by simply placing PDMS plate on the chip.

Although the above description describes binding the top plate with the electrorotation chip, the plate and the electrorotation chip could also be formed from one piece of substrate material. For example, microelectrode elements in multiple electrorotation units are micro-fabricated or processed on the substrate material. Then, photolithography-based etching may be applied to etch away the central regions of the electrorotation units to form thin wells (e.g., 10–20 microns). Particles placed in these wells are exposed to rotating fields when electrical signals are applied to the electrode elements.

The electrorotation assay chamber can then be incorporated into a high-throughput electrorotation assay system as described in the following example.

EXAMPLE 5

Figure 4:
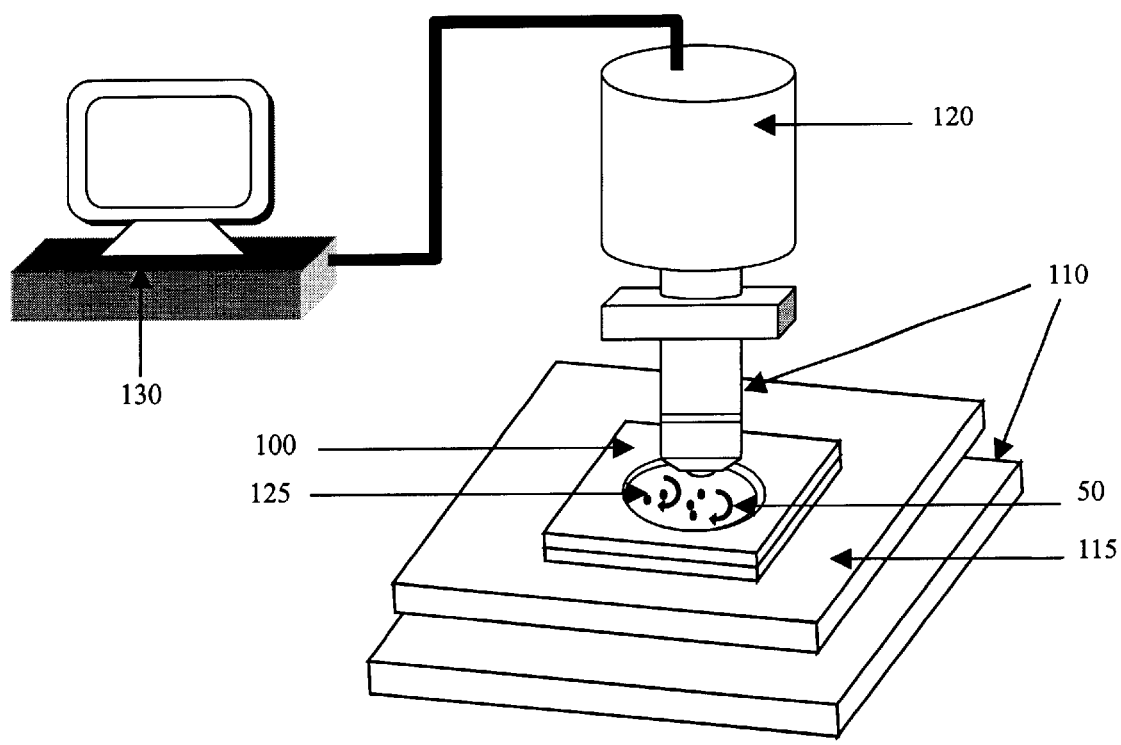
FIG. 4 is a schematic diagram showing an electrorotation assay system consisting electrorotation chamber, optical imaging apparatus and image-analysis/processing devices.

FIG. 4 shows a schematic representation of one embodiment for a high-throughput electrorotation assay system. The system consists of an electrorotation assay chamber 100 that can generate multiple rotating electrical fields on the chip when appropriate electrical signals are applied. The chamber 100 is placed on a microscope stage 115. The optical microscope 110 coupled with an imaging camera 120 is used to obtain the electronic images of the particles 125 in rotating fields. The electronic image signals from the camera are captured and processed by a computer 130 to determine particle rotational behavior (rate and direction). The particle rotation responses are then analyzed to derive particle electrical parameters and to obtain different assay results.

Particle rotation response is affected by the structure of the electrorotation unit. The following example shows an embodiment where the electrode elements have a butterfly footprint.

EXAMPLE 6

FIG. 5 shows a schematic drawing of one embodiment for a high-throughput electrorotation chip. Four electrode elements 140 having butterfly footprints form one electrorotation unit on the substrate 145. The electrode elements in different units are electrically connected through horizontal conductors 150 and vertical conductors 160. The electrode elements and conductors that are electrically connected together have the same shading. The horizontal conductors 150 are connected together at the regions outside the electrorotation units through major vertical conductors 158. Similarly, the vertical conductors 160 are connected together at the regions outside the electrorotation units through major horizontal conductors 168. Corresponding electrode elements of all the electrorotation units are connected together. Each electrorotation unit comprises four electrode elements. There are four major electrode conductors (two vertical conductors 158 and two horizontal conductors 168) that are connected separately to four electrode pads at the peripheral regions of the chip. Thus, only four electrode pads 170 are needed to connect electrical signals from external signal generators to all the electrorotation units. The signal generator can produce waveforms such as a sinusoid having phase offsets of 0, 90, 180 and 270 degrees. The four signals are routed to the four electrode elements of the electrorotation units. Insulation dielectric layers may be incorporated over the horizontal and/or vertical lines so that the conductors carrying different electrical signals are not connected. Multiple-layer photolithography (i.e., multiple optical masks are required) may be used for making such a chip so that the horizontal conductors and the vertical conductors are fabricated in different layers of the substrate. For example, with a silicon substrate, the vertical conductors may be fabricated through phosphate-doping of the silicon to achieve desired electric conductivity. A dielectric layer may then be built over the vertical conductors. Then a metal film (e.g., Au, Al) may be deposited over the dielectric layer to form electrode elements and horizontal conductors using photolithography. In this way, the electrorotation units in FIG. 5 may be realized using two conductive layers. Electrical connections between the two conductive layers may be realized using the "electrically-conductive-vias" through the insulating layer. The steps for fabricating such "vias" may involve etching through the insulation layer at required positions to form "holes" and then electroplating through the holes. Those skilled in the art of microfabrication can choose and determine appropriate protocols and procedures for fabrication. The size of the electrorotation units is in the range between 1 micron and 1 cm, and preferably between 20 microns and 2 mm. The electrorotation unit size depends on the size and geometry of the particles to be analyzed.

The electrode elements may also have alternate shapes and layouts as explained below.

EXAMPLE 7

Figure 6:
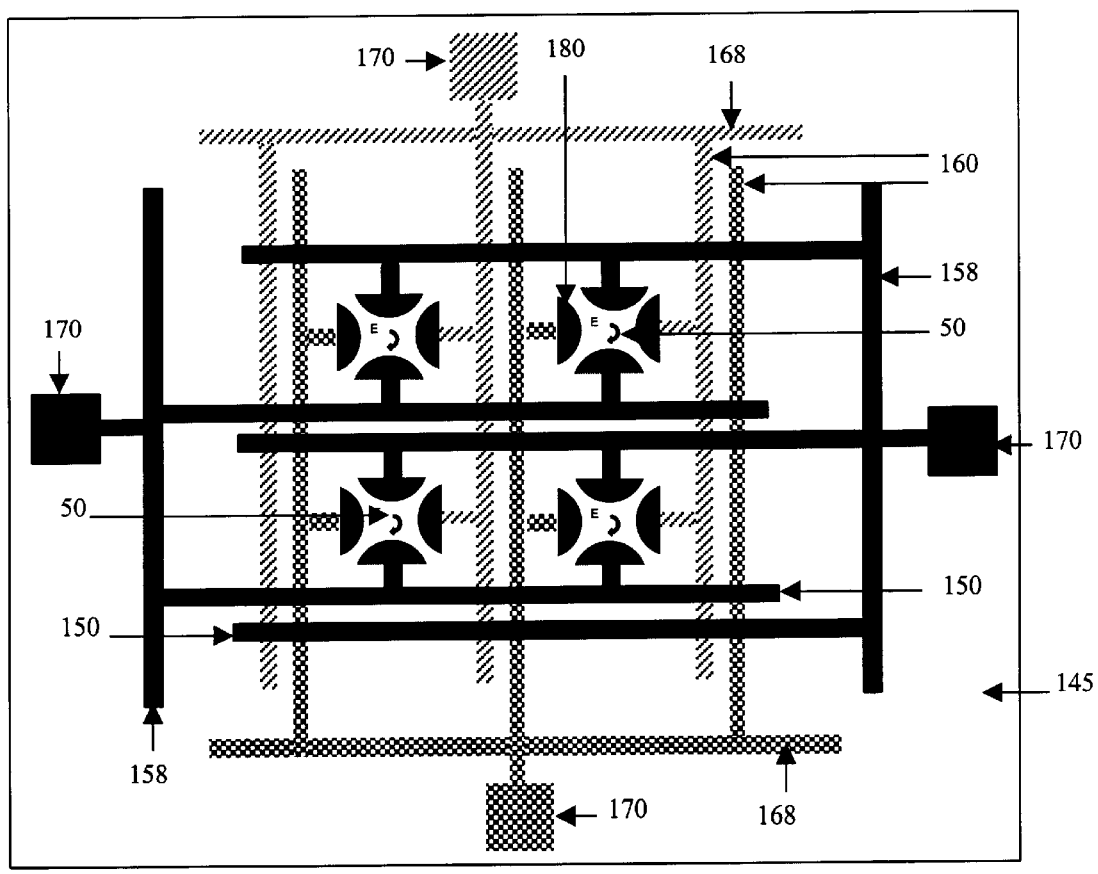
FIG. 6 shows a high-throughput electrorotation assay chip having electrode elements each comprising arcs facing towards the center of the electrorotation unit.
Figure 7:
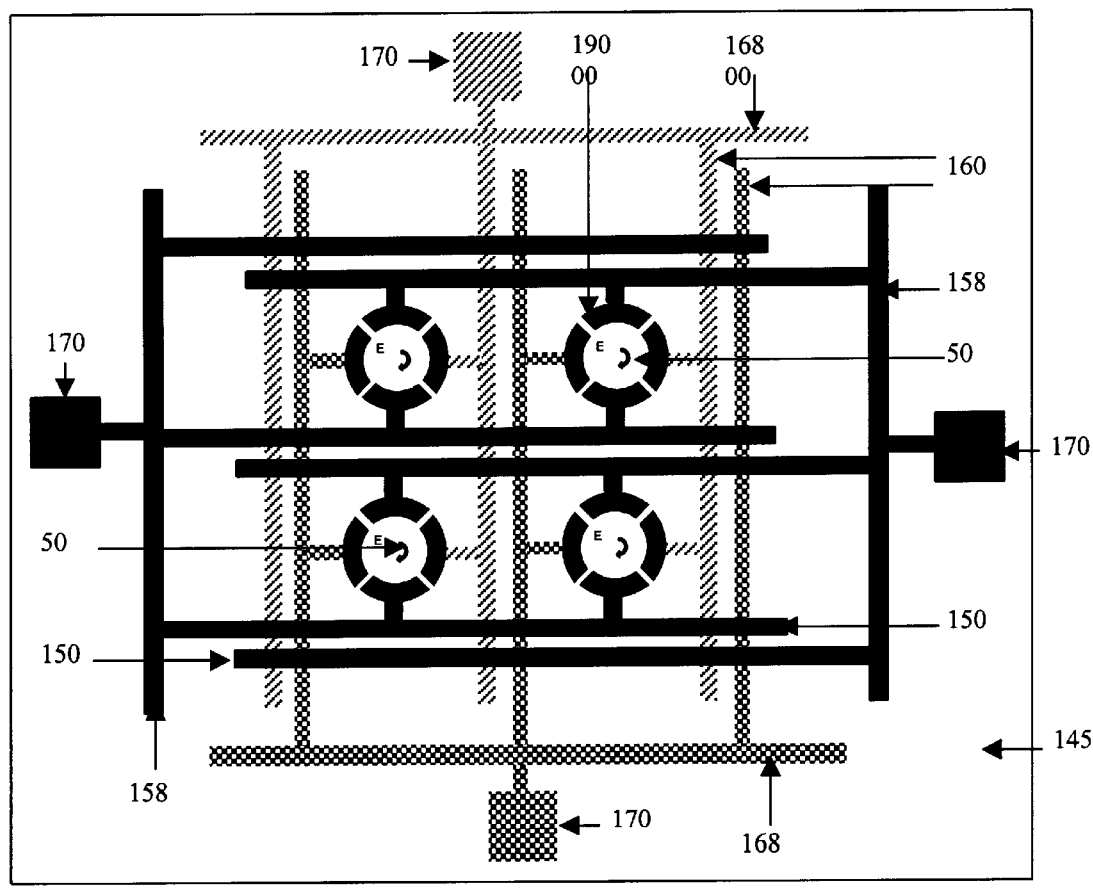
FIG. 7 shows a high-throughput electrorotation assay chip having electrode elements comprising arcs facing away from the center of the electrorotation unit.
Figure 8:
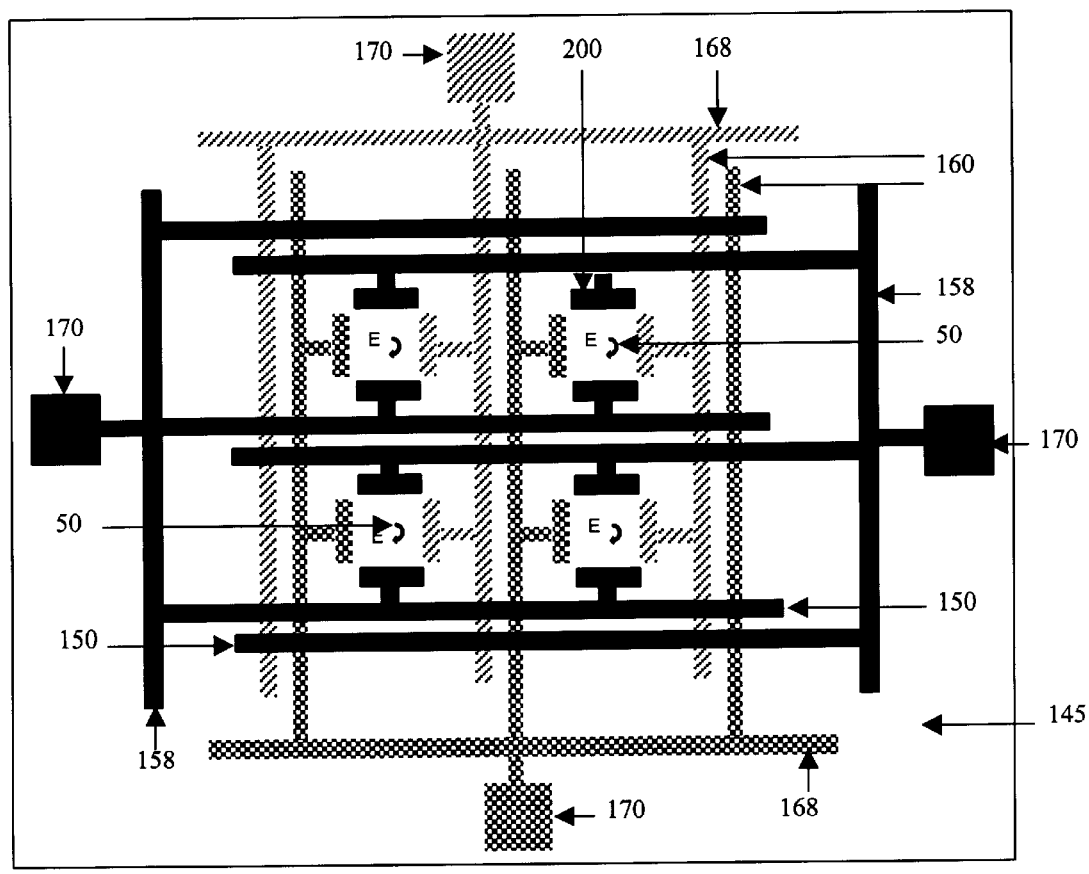
FIG. 8 shows a high-throughput electrorotation assay chip having linear electrode elements.

FIGS. 6, 7 and 8 show three other embodiments of electrode structures where the electrode elements have convex, concave and linear footprints, respectively. The size of an electrorotation unit is in the range between 1 micron and 1 cm, and preferably between 20 microns and 2 mm. Except for their different electrode structures, these assay chips are similar to the electrode chip of FIG. 5, and may be fabricated using multiple-layer photolithography. For the electrode elements shown in FIGS. 6, 7 and 8, the distance between the two opposite electrode elements can vary between 1 micron and 5 mm. Except for their different electrode structures, these assay chips are similar to that of FIG. 5. These chips may be fabricated using multiple-layer photolithography.

The assay chips shown in FIGS. 6, 7 and 8 have the advantages of high throughput capabilities, relatively easy fabrication process and simple electrical connection between the electrode elements and the external signal generators. The high throughput capability is determined by the size and density of the electrorotation units. Multiple-layer photolithography may be used to fabricate these electrodes using a two-conductive-layer structure. Because all the corresponding elements in each unit are electrically connected together, only four electrode pads are required for energizing all the electrorotation units.

Figure 9:
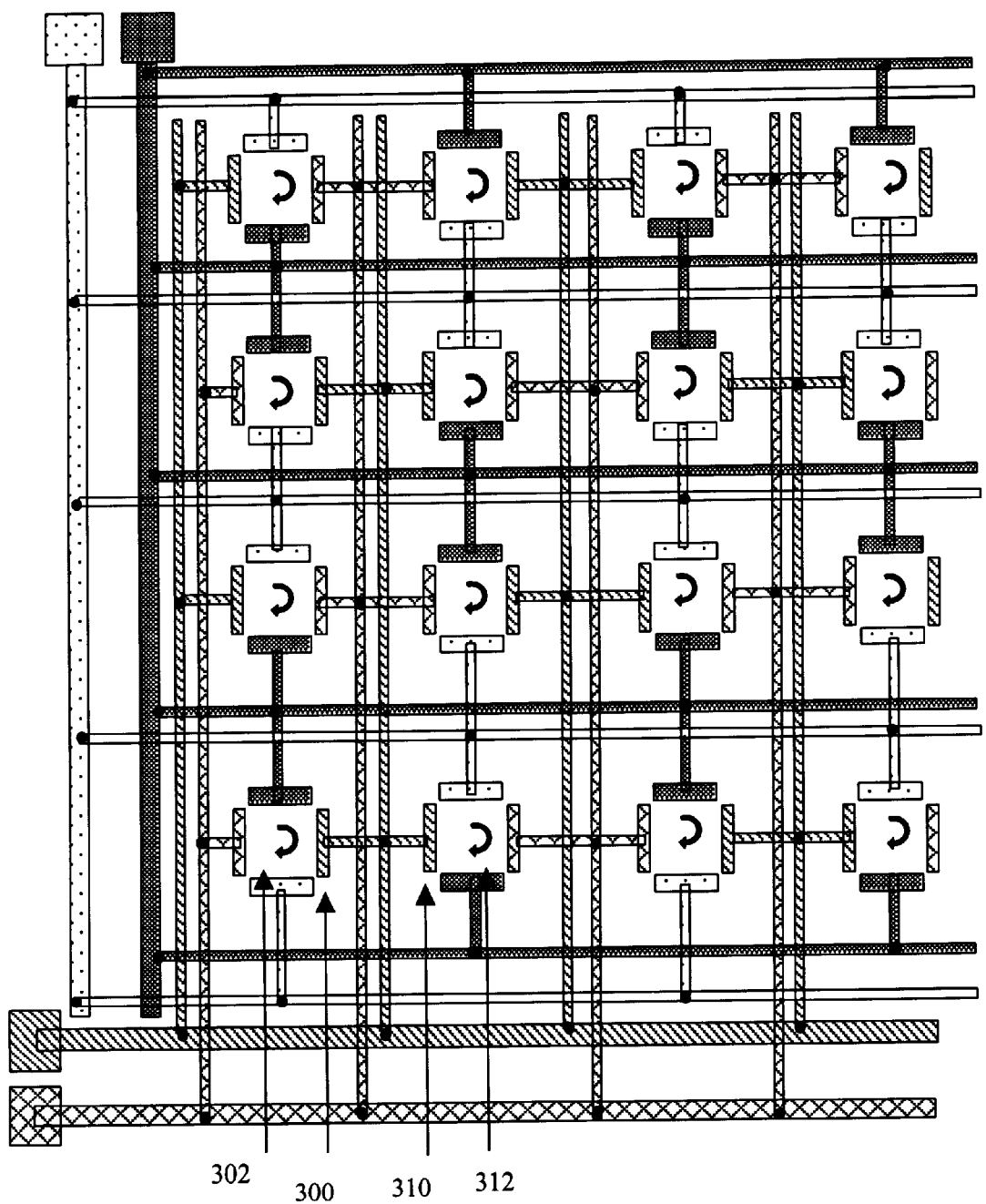
FIG. 9 shows a high-throughput electrorotation assay chip where adjacent electrode elements from adjacent electrorotation units are electrically connected together.

FIG. 9 shows a schematic drawing of an electrode structure wherein the electrode elements are placed such that adjacent electrodes 300 and 310 from adjacent electrorotation units 302 and 312 are electrically connected together. The adjacent placement of electrically connected electrode elements simplifies the fabrication process. Because adjacent electrodes 300 and 310 are electrically connected and carry the same signal, cross-talk between adjacent electrorotation units is reduced.

Figure 10:
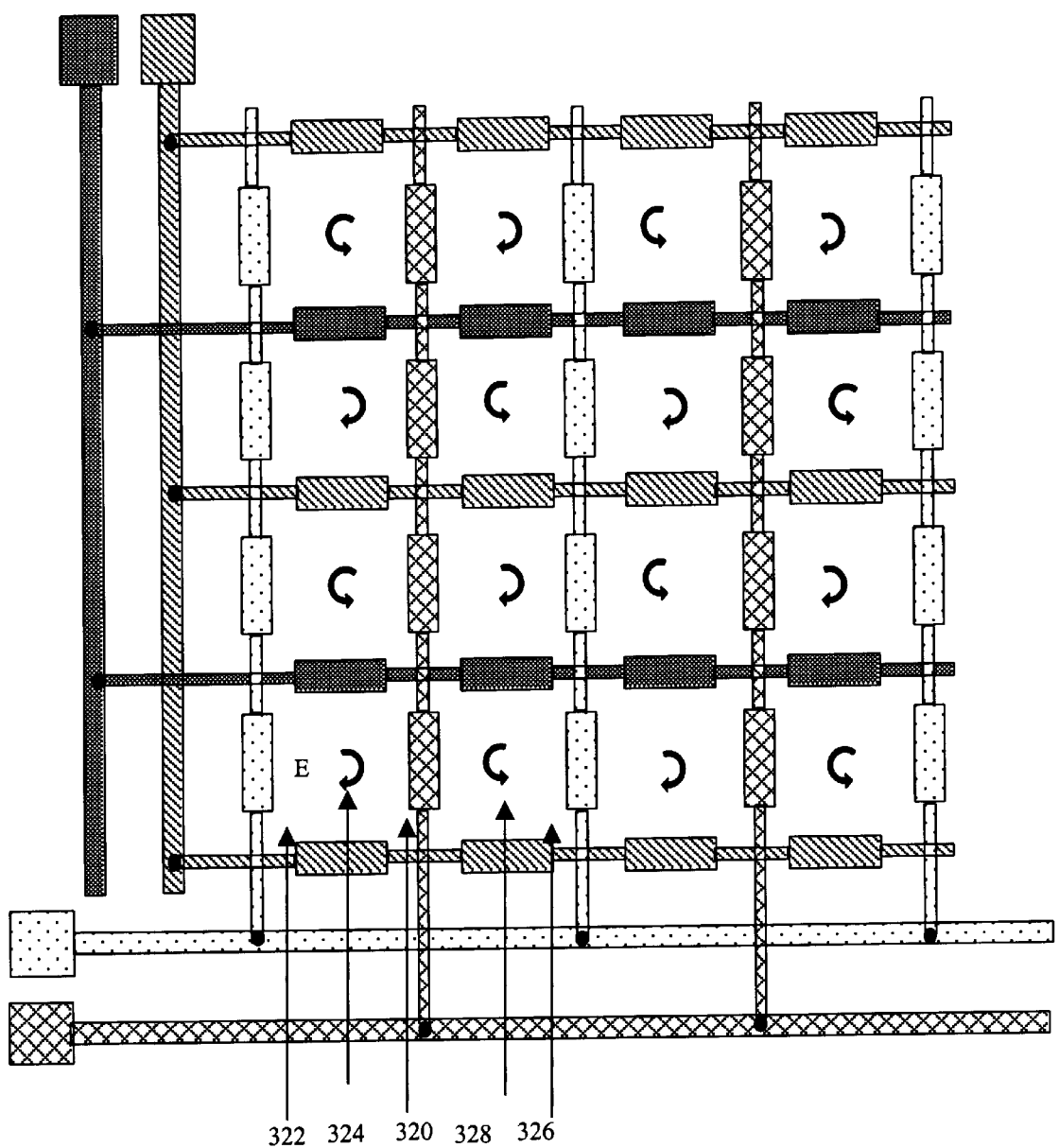
FIG. 10 shows a high-throughput electrorotation assay chip having adjacent electrorotation units that share electrode elements. The electric field in adjacent electrorotation units rotates in a reverse direction.

FIG. 10 shows a schematic drawing of an electrode structure wherein the electrode elements are placed such that a single electrode 320 is shared by adjacent electrorotation units 322 and 326. This placement causes the electric field 324 of electrorotation unit 322 to rotate in a reverse direction from the electric field 328 of adjacent electrorotation unit 326. Because the rotation of electric field 324 is reversed from the rotation of electric field 328, the electric fields 324 and 328 rotate in a parallel direction at the boundary of the adjacent electrorotation units 322 and 326 which in turn reduces the cross-talk between adjacent units. The sharing of the single electrode 320 by adjacent electrorotation units 322 and 326 simplifies the fabrication process.

Figure 11:
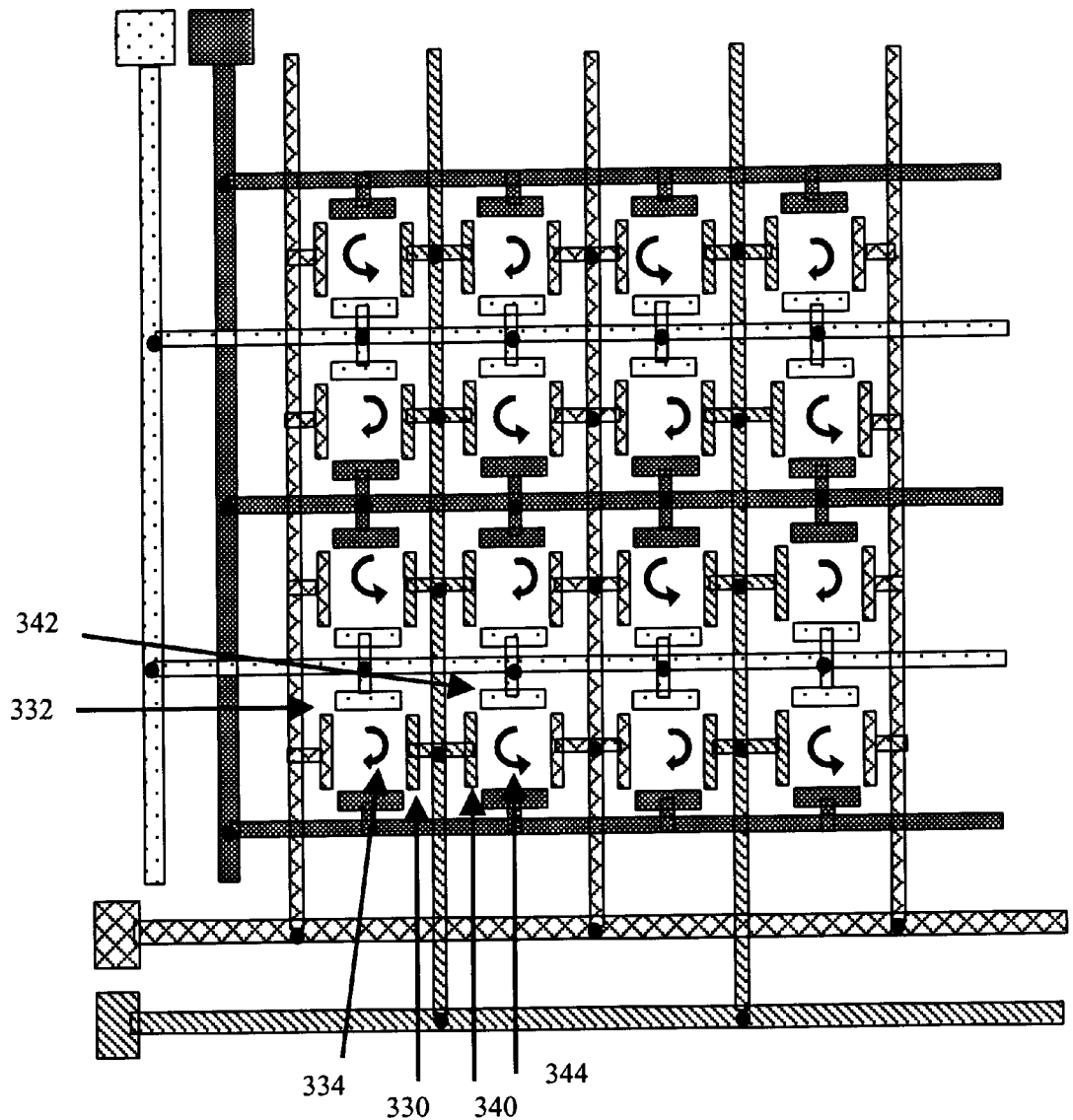
FIG. 11 shows a high-throughput electrorotation assay chip where adjacent electrode elements from adjacent electrorotation units are electrically connected together. The electric field in adjacent electrorotation units rotates in a reverse direction.

FIG. 11 shows a schematic drawing of an electrode structure wherein the electrode elements are placed such that adjacent electrodes 330 and 340 from adjacent electrorotation units 332 and 342 are electrically connected together. This placement causes the electric field 334 of electrorotation unit 332 to rotate in a reverse direction from the electric field 344 of adjacent electrorotation unit 342. Because the rotation of electric field 334 is reversed from the rotation of electric field 344, the electric fields 334 and 344 rotate in a parallel direction at the boundary of the adjacent electrorotation units 332 and 342 which in turn reduces the cross-talk between adjacent units. The placement of electrically connected electrodes 330 and 340 to be adjacent simplifies the fabrication process.

Where the electric fields rotate in different directions, the imaging system must compensate for the corresponding change in particle rotation. One way to accomplish this is to flip the image either horizontally or vertically before measuring particle movement in electric fields with a reversed rotation. Compensation can also be used in the algorithms that determine particle movement.

Figure 12A:
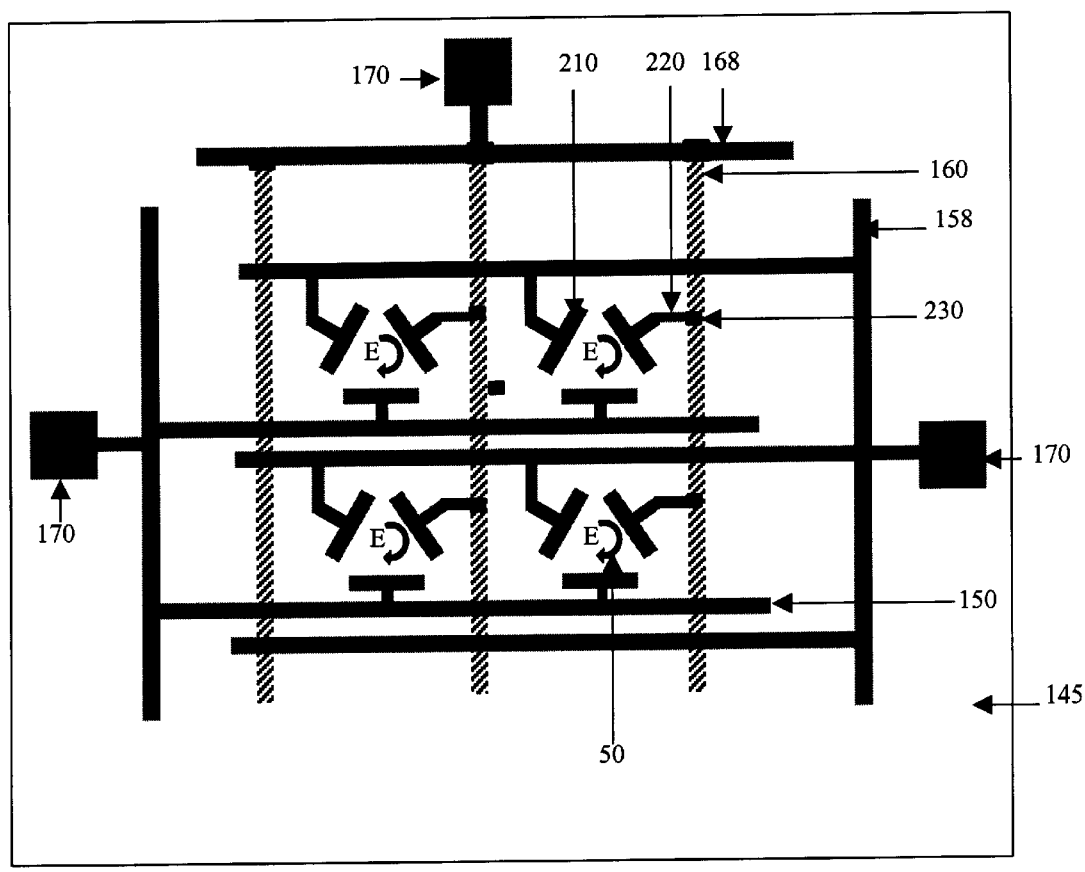
FIG. 12(A) shows a high-throughput electrorotation assay chip where every signal input is electrically connected to one electrode element within each electrorotation unit and the three linear electrode elements uniformly spaced about the center of each electrorotation unit are electrically insulated.
Figure 12B:
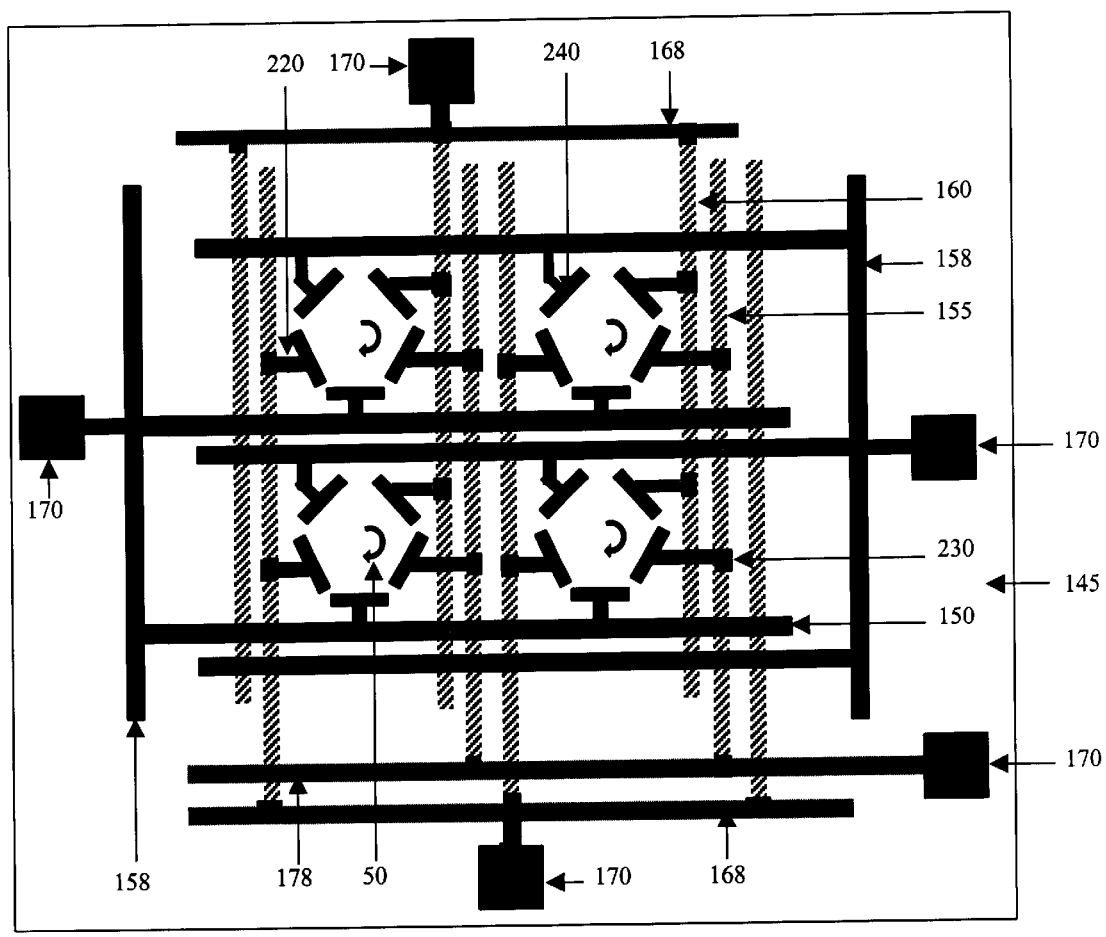
FIG. 12(B) shows a high-throughput electrorotation assay chip where every signal input is electrically connected to one electrode element within each electrorotation unit and the five linear electrode elements uniformly spaced about the center of each electrorotation unit are electrically insulated.
Figure 12C:
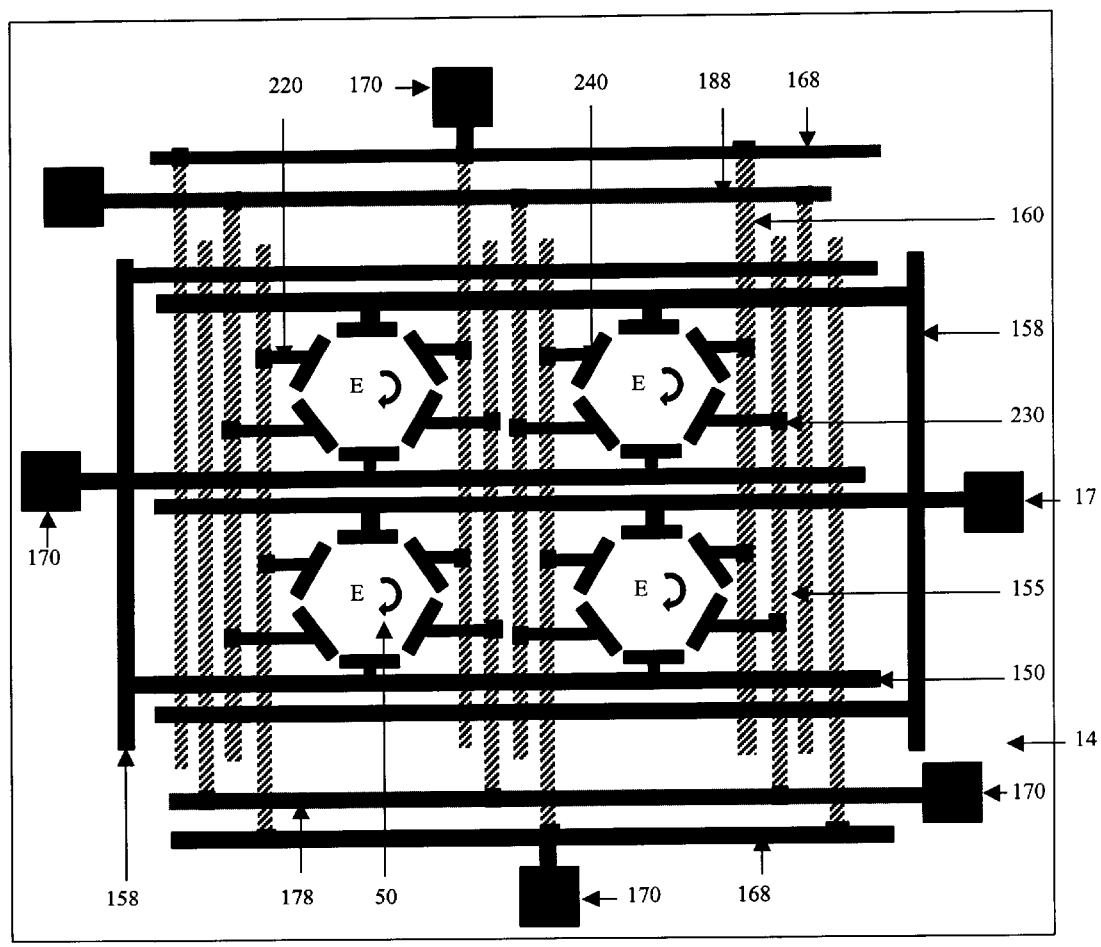
FIG. 12(C) shows a high-throughput electrorotation assay chip where every signal input is electrically connected to one electrode element within each electrorotation unit and the six linear electrode elements uniformly spaced about the center of the electrorotation unit are electrically insulated.

FIGS. 12(A), 12(B) and 12(C) show electrorotation units having three, five and six linear electrode elements. The electrode elements and conductors that are in the same layer of the substrate have the same shading.

The layout for each embodiment can be accomplished using two conductive layers. For example, in FIG. 12(A) the first layer comprises the vertical conductors 160, while the second layer comprises the electrode elements 210, the horizontal conductors 150, the major conductors 158 and 168, and the electrode connectors 220. In FIG. 12(B) the first layer comprises the vertical conductors 160, while the second layer comprises the electrode elements 240, the horizontal conductors 150, the major conductors 158 and 168, and the electrode connectors 220. In FIG. 12(C) the first layer comprises the vertical conductors 160, while the second layer comprises the electrode elements 250, the horizontal conductors 150, the major conductors 158, 168, 178 and 188, and the electrode connectors 220. An insulation layer separates the two conductive layers.

All the electrorotation units may be connected in parallel and energized together. Alternatively, electrorotation units may be individually addressable or addressed in such a way that some electrorotation units are connected in parallel. In these cases, switches may be used to address electric signals from signal generators to electrode elements in which it is desired to generate a rotating electrical field.

Selective addressing of individual units can be achieved in a number of ways. For example, an electronic switch may be used to connect the electrical signal to an electrode element on the chip. An additional electrical signal may be used to control the switch on/off status. Alternatively, a mechanical switch may be used to manually turn on or turn off the electrode elements. In both approaches various combinations of energized electrorotation units may be achieved.

Figure 13:
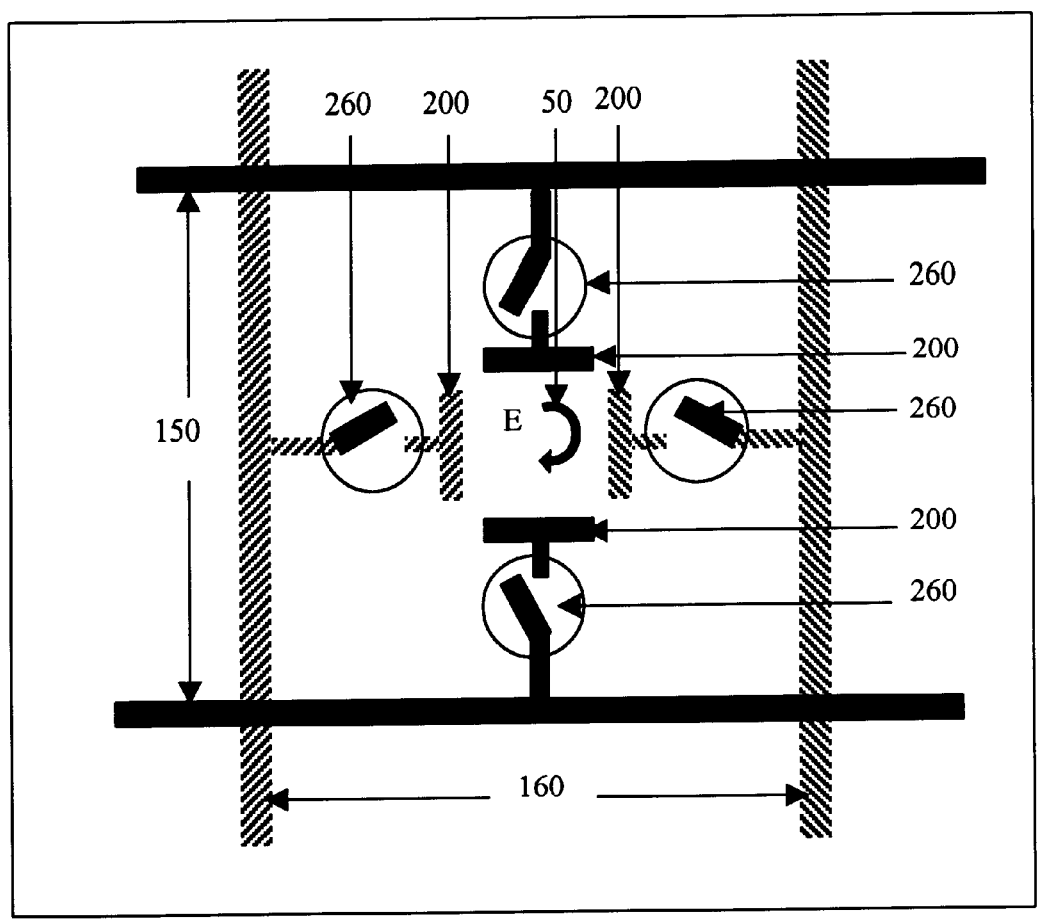
FIG. 13(A) is a schematic diagram showing the principle of addressing individual electrorotation units by using electric switches.
FIG. 13(B) shows an electric switch that is a bipolar transistor.
FIG. 13(C) shows an electric switch that is a MOSFET (Metal-Oxide-Semiconductor-Field-Effect-Transistor).
Figure 13:
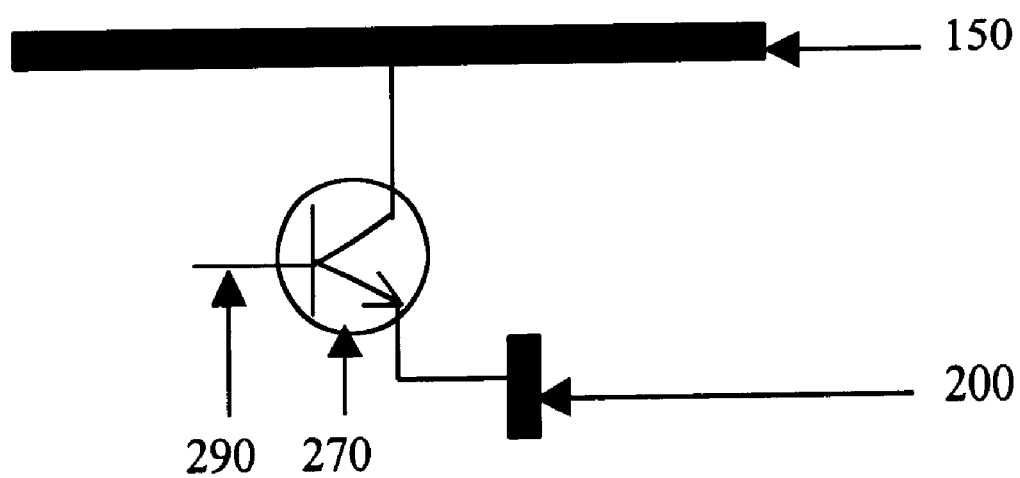
Figure 13:
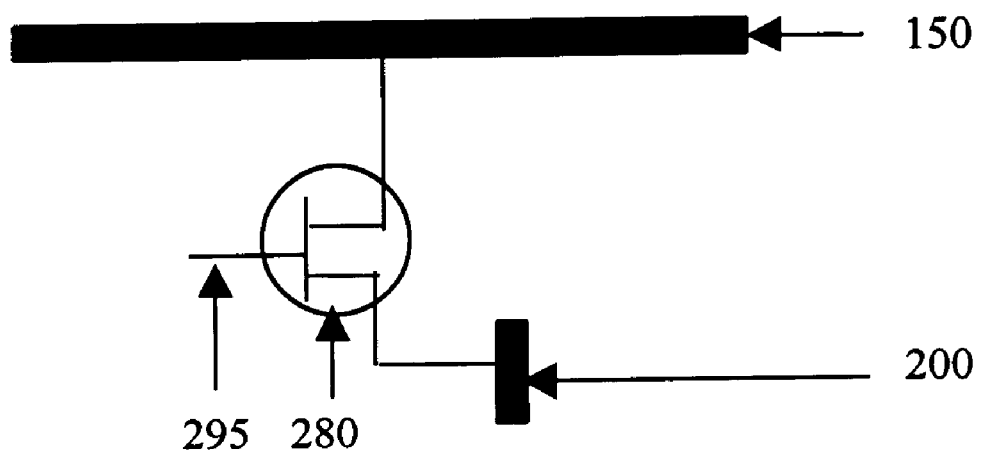

FIG. 13(A) shows the addressing of individual electrorotation units by using electric switches. Each electrode element 200 within an electrorotation unit is connected through a separate switch 260 to the electric signal. An electric switch can be, for example, a bipolar transistor 270 as shown in FIG. 13(B), or a MOSFET 280 (Metal-Oxide-Semiconductor Field-Effect-Transistor) as shown in FIG. 13(C). Thus, the electric potential applied to the base 290 of the bipolar transistor or to the gate 295 of the MOSFET determines the on/off status of these electric switches. When appropriate control signals are applied to the electric switches, the switches can be turned on or off so as to connect or disconnect the electrical signals to the electrode elements. The switches for the electrodes within one electrorotation unit are controlled by the same electrical control signal. Because the same control signals are used to switch all the elements within a unit, electrical signals are connected to these electrode elements simultaneously. Thus a rotating field can be turned on or off in each addressable unit.

These transistors can be readily fabricated using fabrication techniques similar to those used for producing the electrorotation units. The transistors can be integrated with the conductors of the electrorotation units using the same substrate.

Alternatively, other forms of electronic switches may be used. For example, the electronic switches used to address individual memory units in an electronic memory chip may be used. These switches may also be fabricated using microfabrication techniques into the same substrate on which electrorotation units are produced. Switches may also be made using emitter-coupled pairs of bipolar transistors.

For fabricating electrorotation chips, the substrate materials may be silicon, glass, silicon dioxide, ceramics or even plastics. The substrate can be made of porous or non-porous materials. Similarly, the material for the insulation layer may include but is not limited to silicon dioxide, aluminum oxide, silicon nitrate, plastics, glass, photoresist, ceramics. The conductive traces may be aluminum, gold, tin, copper, platinum, palladium, carbon, semiconductor materials or composites of the above materials. Similarly, other configurations of the electrode elements are possible. Various microfabrication methods may be employed for producing an electrorotation chip. Fabrication steps such as electron beam evaporation, sputtering, vacuum evaporation, electrode plating and photolithographic patterning may be involved in such fabrications.

Those who are skilled in the art of microfabrication and micromachining may choose appropriate fabrication protocols and materials to fabricate the electrorotation chips.

For example, thin-film printing methods may be used for fabricating the electrorotation assay chips on ceramic materials. Such a printing method has a resolution of 10 microns and can print not only electrically conductive strips but also electrically-insulating lines. Thus, electrorotation chips with multiple conductive-layers may be fabricated. Some advantages of ceramics-based microchips include their robustness, durability, and relative in-expensiveness.

Standard photolithography methods may be employed to fabricate electrorotation assay chips for substrate materials such as glass and silicon. There are a number of variants to this method. As an example, we describe a method to pattern metallic film microelectrodes on a glass substrate. The substrate is pre-coated with a thin metal film layer (e.g., <1 micron) using methods of sputtering or evaporation. A mask with desired patterns is produced using various standard mask-generation methods such as electron-beam writing and laser ablation. Typically, there is a thin film of material on the mask that blocks optical light of specific wavelengths. Regions of the film are removed to produce the desired patterns on the mask.

The transfer of patterns from the masks to the glass substrate chip is achieved with the following approaches. The metal-coated substrate is coated with a thin film of photo-resist, and is then exposed to a light source with the mask placed in direct contact with the substrate. After the light exposure, the photo-resist film on the substrate is developed in an appropriate developing solution so that the regions exposed to the light are developed (or the regions that have not been exposed with the light are developed, depending on the nature of the photo-resist). The metal film on the substrate is then etched in an etching solution so that the regions that are not covered with a photo-resist layer are etched away whilst the regions with the photo-resist coverage are not etched away and protected. Thus, the patterns on the mask are transferred to the metal film layer on the glass substrate. Variations of the procedure described above may be used for generating patterned, thin-film structures of various types (e.g., dielectric films). Surface contact-printing methods may also be used to produce high-throughput electrorotation assay chips on different substrate materials including plastics, ceramics and silicon.

The example below describes a general approach for high throughput electrorotation analysis.

EXAMPLE 8

Figure 14:
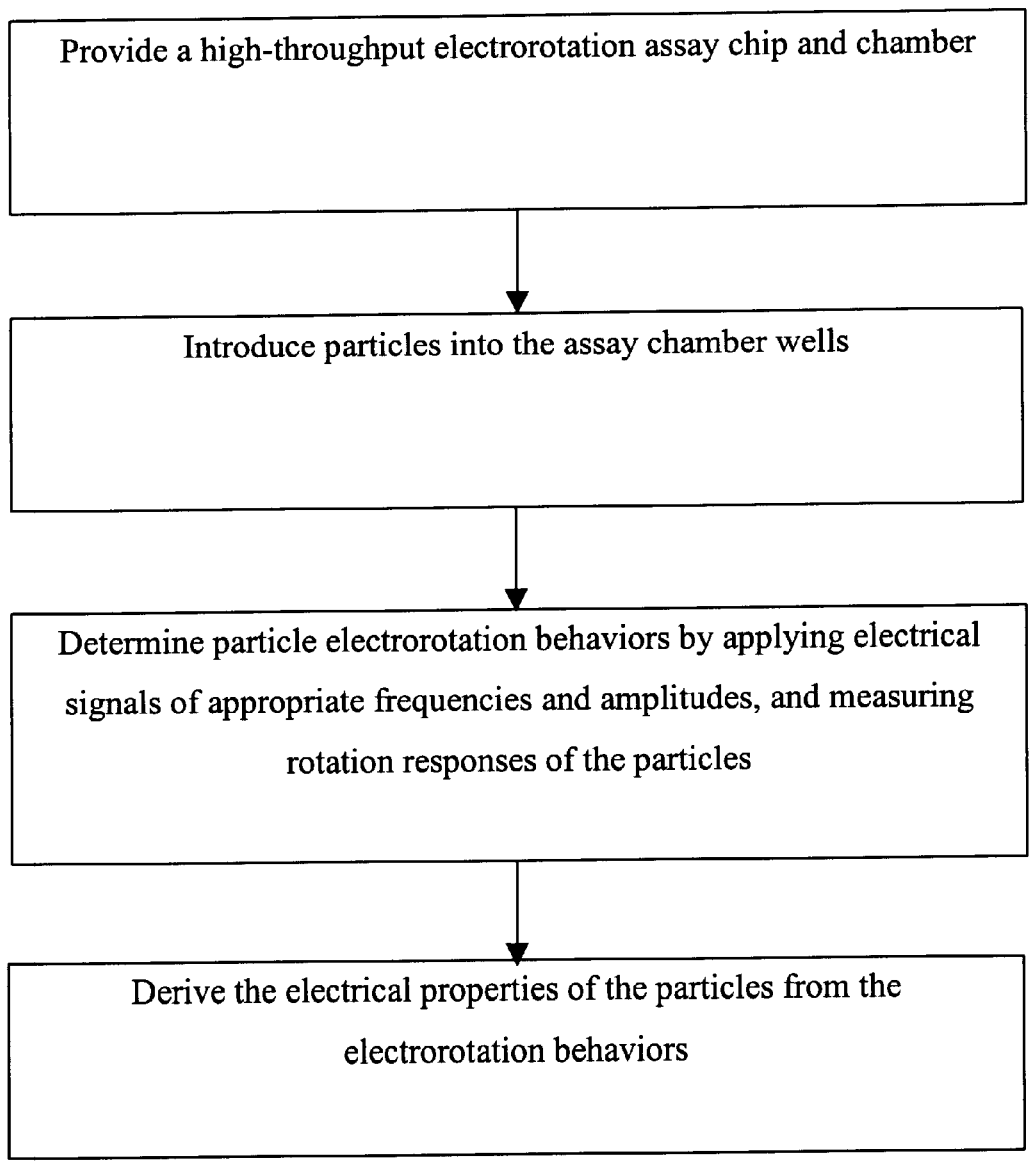
FIG. 14 shows a flow chart for a typical high-throughput electrorotation assay.

This example provides a general approach for the operation of the electrorotation assay chip embodiments. A flow chart is provided in FIG. 14. At the outset, a high-throughput electrorotation assay chip and assay chamber is fabricated. The choice of chip and chamber configuration is determined by the intended use. For example, a chamber with one assay well may be used for the analysis of a homogeneous or heterogeneous population of particles of different types in a single suspension. For an assay in which different types of particles are suspended in different solutions, a chamber with multiple assay wells may be used.

Once the device is constructed, the particles for analysis are introduced into the assay chamber wells. With the chamber having one assay-well, a particle suspension consisting of different types of particles is loaded into the well. With a chamber having multiple wells and an assay involving multiple particle types in multiple assay solutions, one particle type is loaded into each assay well. Various loading methods may be used (e.g., the chamber wells can be loaded sequentially or simultaneously). A single sample-dispensing-head may also be used to dispense particles one type at a time. Alternatively, multiple sample-dispensing-heads may be used in combination to dispense multiple types of particles simultaneously. Commercially available sample-dispensing heads are suitable for most embodiments, however, one of skill can readily construct sample dispensing heads that are optimal for a particular use or assay format. Preferably, the sample dispensing volume is between about a nanoliter and several hundreds of microliters, however, the dispensing volume can exceed 1 ml in some embodiments. That is, the sample dispensing volume can be about 1 nl, 5 nl, 10 n, 50nl, 100 nl, 1 $\mu$l, 10 $\mu$l, 200 nl, 300 nl, 400 nl, 500 nl, 600 nl, 700 nl, 800 nl, 900 nl, 1 $\mu$l, 10 $\mu$l, 100 $\mu$l, 200 $\mu$l, 300 $\mu$l, 400 $\mu$l, 500 $\mu$l, 600 $\mu$l, 700 $\mu$l, 800 $\mu$l, 900 $\mu$l or in some cases 1 ml or more.

Once the sample(s) has been loaded, electrical signals at various frequencies and amplitudes are applied to the electrode elements in electrorotation units. At each frequency, the electrorotation behaviors (e.g., rotation rate and direction) of particles of different types are determined. For the case where particles of various types are mixed together, when an individual particle is measured, not only its rotation behavior but also its type is determined, allowing an association between particle types and their rotation responses. For the case where individual particles in each well belong to one group, the rotational responses of selected particles are measured. If statistical analysis is to be performed, desirably, the number of particles to be analyzed and characterized for each type is greater than 5 and, preferably, is between 10 and 100. Depending on the algorithm used, the rotation rates of multiple particles can be determined simultaneously.

Once the electrorotation measurements of the particles are made, the electrical properties that correspond to these measurements are derived using analysis and simulation methods. Different analytical approaches can be used to obtain the electrical parameters for the different particles. For example, mammalian cells can be modeled with shelled spheres in a shell model. The shells can be made to correspond to the cell membranes, cytoplasm, and nuclear membranes. The derived parameters can reflect cell membrane conductance and capacitance, or nuclear membrane conductance and capacitance, or conductivity and permittivity of cytoplasm and nuclease interior. Different applications can focus on the electrical properties of different compartments of the cells. In a number of cases, the electrical properties of the cell membrane are sensitive markers of cell physiological states, and, thus, membrane capacitance and/or conductance values are derived. Those skilled in the art can readily determine the models that would be most applicable to the types cells that are being measured. For further reference see e.g., (Interpretation of electrorotation of protoplasts I: the theoretical consideration by Fuhr G, Gimsa J, Glaser R, *Stud. Biophys.* 108: 149–164, 1985, herein expressly incorporated by reference in its entirety; Theory and application of the rotation of biological cells in rotating electric field by Gimsa J, Glaser R and Fuhr G in *Physical characterization of biological cells*, Schutt W, Klinkmann H and Laprecht I and Wilson T editors, Gesundheit, Berlin, pp 295–323, 1991, herein expressly incorporated by reference in its entirety; Differences in the AC electrodynamics of viable and non-viable yeast cells determined through combined dielectro-phoresis and ROT studies by Huang Y, Holzel R, Pethig R and Wang X-B *Phys. Med. Biol.*, 37: 1499–1517, 1992, herein expressly incorporated by reference in its entirety; and Numerical analysis of the influence of experimental conditions on the accuracy of dielectric parameters derived from ROT measurements by Gascoyne P R C, Becker F F and Wang X-B, *Bioelectrochem. Bioenerg.* 36:115–125, 1998, herein expressly incorporated by reference in its entirety).

Non-biological particles can also be evaluated by using models. The models for microbeads of homogeneous compositions, for example, involve surface and bulk dielectric properties. Typically, dielectric parameters of particle bulks are known and the assay focuses on the surface properties of the particles, e.g., surface conductivity and permittivity. The analyses of electrorotation responses can be automated and dielectric parameters may be derived and displayed in a digital format. A device and approach that was used to evaluate the electrorotation properties of yeast cells is provided in the following example.

EXAMPLE 9

Electrorotation chips suitable for the analysis of eukaryotic cells were fabricated and used to determine the electrorotation behavior of a heterogeneous population of yeast cells. The electrorotation chip with electrorotation units as shown in FIG. 5 was built. The characteristic dimension of each unit (the distance between the opposite electrode elements) had varying values of 80, 160 and 320 microns. The distance between the neighboring electrorotation units also varied from 80, 160 and 320 microns. The two conductive layers for the electrorotation chip were silicon doped with phosphors and aluminum film. An electrorotation chamber was constructed by gluing the top portion of an eppendorf tube (diameter ~5 mm, height 1 mm) to an electrorotation chip. After pipetting an aliquot of cell suspension sample into the chamber, the chamber was then sealed with a top glass slide. The cell rotation behavior was examined under microscopy coupled with a CCD camera and a TV monitor.

Samples of yeast cell suspensions were then examined with the electrorotation chip. Yeast cells were cultured using standard cell culture methods. The yeast cells were first harvested and then resuspended in a 8.5% sucrose buffer whose electrical conductivity was adjusted to be between 100 $\mu$S/cm and 1000 $\mu$S/cm. When the cell populations were subjected to rotating fields between 1 kHz and 10 MHz, it was observed that a subpopulation of the cells exhibited rotation in the frequency range while other cells exhibited little or no rotation. These two cell populations were then analyzed using light microscopy. The first population was light-colored and exhibited rotation while the second population was dark-colored and exhibited little or no-rotation. The electrorotation frequency spectrums of the cells in the two populations were measured and were used to derive the electrical properties of the cells. The example below describes an approach to rational drug design that employs an electrorotation device that has multiple electrorotation chambers.

EXAMPLE 10

Figure 15:
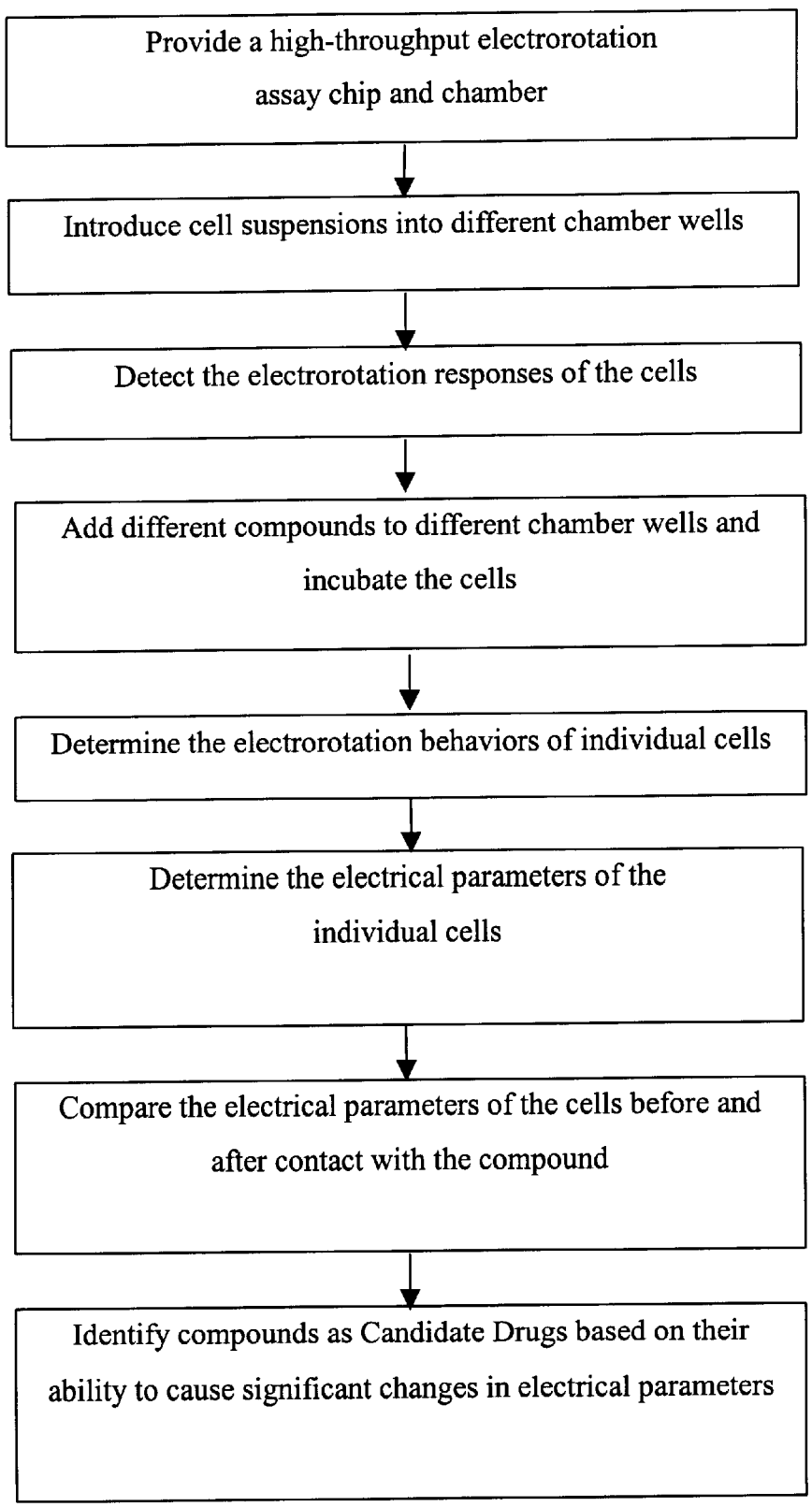
FIG. 15 shows a flow chart for a rational drug screening approach that uses a high throughput electrorotation assay.

This example teaches the use of a high throughput electrorotation assay to screen compounds from a chemical library for their interaction with a particle of interest. (See FIG. 15). The assay is designed to identify molecules that interact with a target on or in a cell and, thereby, alter the cell's biological state. Preferably, the target molecules are involved in a biochemical pathway (e.g., disease process) and an interaction between the drug and the target molecule affects the biochemical pathway and, in doing so, modifies cellular properties that can be detected by electrorotation analysis. Compounds that cause such changes in a cell's electric properties are then identified as candidate drugs.

For such an application, a proper electrorotation assay chip should be designed with appropriate number of electrorotation units and appropriate dimensions of electrorotation assay chamber wells. For example, a chip having dimensions of 5 cm×5 cm may comprise 1,600 units each occupying a 1 mm×1 mm space in a center region of 4 cm×4 cm would be suitable. The assay chamber is preferably constructed with the same number of wells as the number of the electrorotation units on the chip.

Once the chip has been made, a high-throughput assay is performed. Preferably, mammalian cells are introduced into the electrorotation assay wells. Each well is loaded with approximately the same number of cells in a small volume (e.g., about 100–200 $\mu$l). The cell suspension may be provided in several ways but, preferably, an automatic or semi-automatic sample dispensing head(s) are used. The cell suspension media is carefully chosen so that the cell viability and normal growth are maintained throughout the process.

Next, electrorotation measurements of the cells (i.e., cells that have not yet been exposed to a chemical from the library to be screened) are taken. The unexposed cells are introduced to the wells and then are subjected to rotating electrical fields that are produced at electrorotation units by applying appropriate electric signals. Cell electrorotation behaviors are determined by measuring the rotation rate and direction of individual cells under rotating electrical fields of different frequencies. Frequencies are preferably chosen to reflect the electrical properties to be analyzed. Because the cells in each assay well are essentially similar to each other, only the cells in one or several wells need to be measured and analyzed with suitable dielectric models.

Once the control or baseline measurements have been made, compounds from the chemical library are introduced to the assay wells. Preferably, the different compounds are introduced into the reaction wells at a plurality of concentrations. That is, a titration of each compound is made and the titration of any one compound employs a set of wells and each well within this set has a different concentration of the compound. In this manner the effects of various concentrations of a plurality of compounds on the cells can be rapidly determined. The compounds can be provided to the wells in a number of ways and desirably, an automatic or semi-automatic dispensing head(s) are used. One or more samples may be dispensed each time.

Once the compounds have been provided to the cells, the cells are allowed to interact with the compound for a sufficient length of time. The incubation time can depend on the target and/or the chemicals in the library. A sufficient time can be, for example, from 5 minutes to 24 hours, however, in most assays, the chemicals are allowed to interact with the cells for about 20 minutes. Cell viability and normal growth may need to be maintained during the incubation and the time of incubation can be shortened if viability is compromised by a long-term exposure to a compound. In some embodiments, the composition of the environment in which the chips are placed (e.g., media, gas, and humidity) is controlled to enhance cell viability. Heated platforms, microscope stages, and buffers resistant to temperature fluctuation can be used, for example. Chips with porous supports are also preferred so that the porosity in the chip allows for the exchange of gaseous molecules between the chamber assay wells and their environments.

After a sufficient time of incubation, the cells in each reaction well are subjected to the electrorotation assay. Electrorotation behaviors of the individual cells are determined at various frequencies and an automatic imaging device and image processing algorithms can be applied. The number of the cells that are analyzed for each compound can depend on the library used but, preferably, a sufficient number (e.g., greater than 5 and, preferably, between 10 and 50) is used so that a statistical analysis can be accurately performed. In some embodiments, interaction of a compound with a cell may be detected using agents which bind to the test compound present on or in a cell and which confer a difference in electrorotation properties with respect to cells which have not interacted with the compound.

Next, the cell electrorotation data is analyzed to determine whether the compounds have interacted with the cells or target molecules. Once a statistical analysis of the electrorotation parameters or electrical parameters has been determined, a comparison between the cell parameters prior to and after the incubation of the chemical compounds is made. That is, compounds that interact with the cells or a target molecule on the cell are revealed by observing a statistically significant difference between the control electrorotation measurements and the electrorotation measurements made after contact with the compound. Because the electrorotation units are on an array, e.g., the well number and the compound number are recorded and addressed, the identity and concentration of the chemical that modulates an electrorotation behavior can be identified rapidly. If a significant change was not detected, then the compound is believed to have not interacted with the cells. The example below describes the use of the electrorotation devices and assays described herein to determine the identity and concentration of a target particle in a solution.

EXAMPLE 11

Figure 16:
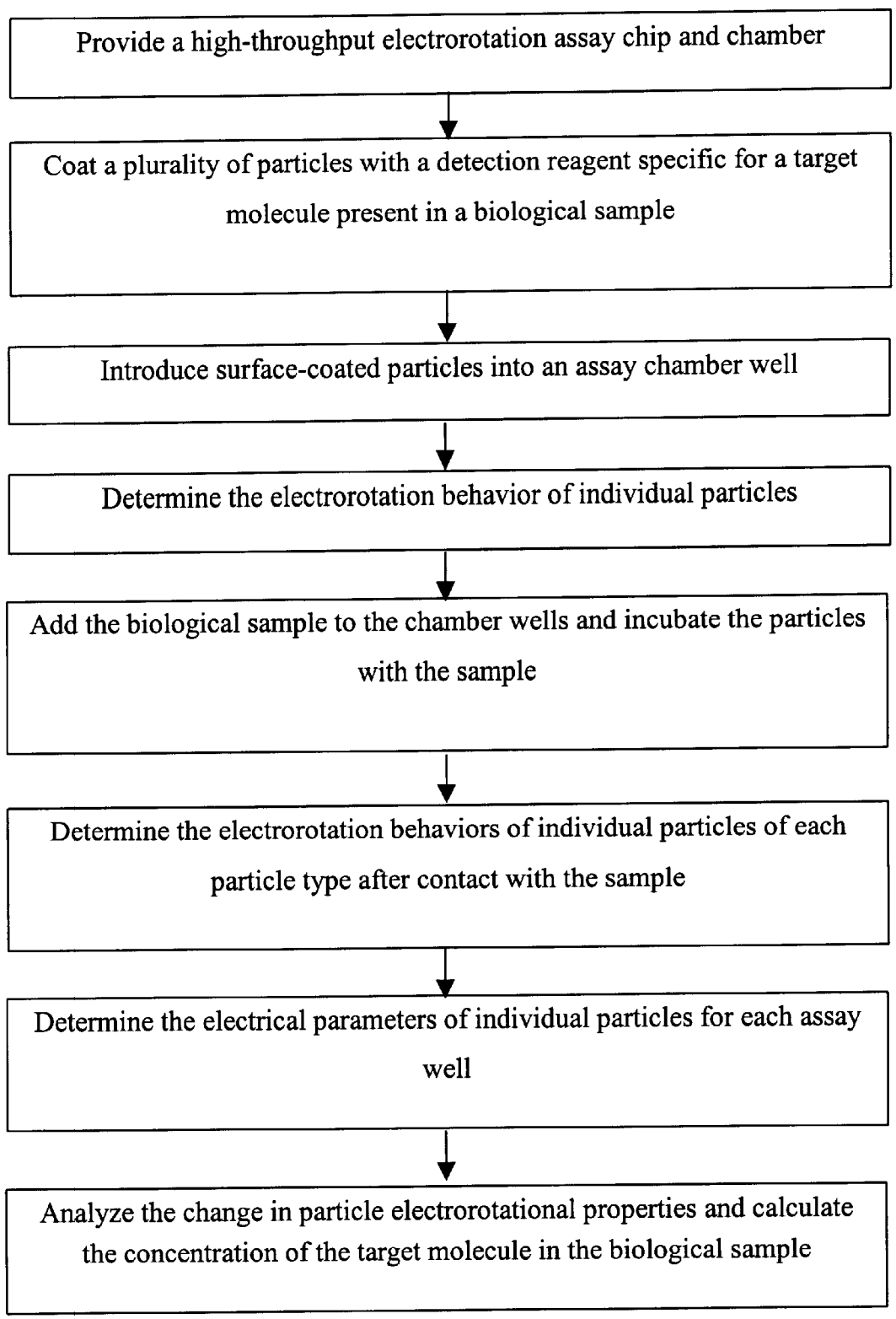
FIG. 16 shows a flow chart for an approach that uses a high-throughput assay to determine the identity and concentration of a target particle in a biological sample.

This example teaches the use of a high throughput electrorotation assay to determine the identity and concentration of a target particle(s) or molecule(s) in a biological sample. (See FIG. 16). The biological sample may contain multiple types of molecules or particles (e.g., proteins, antibodies, antigens, DNA or RNA molecules from a cell lysis solution, or bacteria in a body fluid sample, or cancer cells in a body fluid sample) any one of which can be the target particle. Additionally, multiple target particles or molecules of different types can be detected using the approach described below. To perform this assay, a detection particle (e.g., a microparticle) is coated with a detecting molecule (e.g., a detection reagent such as an antibody, dye, or ligand) that specifically interacts with the target particle in the solution. Multiple detection reagents that interact with different target molecules can be employed in the same assay so long as each detection reagent is coated on a detection particle that is unique to that detection reagent.

To obtain a baseline measurement, the detection particle coated with detection reagent is introduced into assay chamber wells prior to contact with a biological sample. The electrorotation chip may contain one or multiple assay wells for this particular application. Next, the electrical properties of the detection particle with detection reagent are determined using pre-determined frequency range and signal amplitude conditions. Appropriate electrical signals are applied to the electrorotation units to achieve the desired frequency range and signal amplitude conditions. The rotational behavior of the detection particle coated with detection reagent is then measured. The electrical parameters that correspond to the detection particle with detection reagent are calculated from their electrorotation responses. A statistical analysis of the electrical parameters can also be performed to derive average values.

Once the baseline measurements are obtained, an appropriate amount of the biological sample (e.g., 100–200 µl) is added to the chamber assay wells. Depending on the type of sample, concentration or dilution may be necessary. The detection particle with detection reagent is allowed to interact with the target particles in the biological sample for a sufficient time and, following the incubation period, the electrorotation properties of the detection particle with detection reagent(s) is analyzed, as described above. If multiple detection reagents are used in the same assay, a correlation between the type of coated detection particle and the observed electrorotation behavior is established.

Next, the electrical parameters measured for the detection particle with detection reagent before contact with the biological sample and the electrical parameters for the detection particle with detection reagent measured after contact with the biological sample are compared. Statistical analysis can also be performed. Based on the magnitude of change in the statistical data for each coated detection particle used, the type and concentration of the target particle(s) in the biological sample can be determined. Those skilled in electrorotation and chemical reaction kinetics can readily derive equations and theories linking the concentration of the molecules in the solution, the surface density of the detecting molecules on the particles, the equilibrium binding constant between the molecules in the solution and the detecting molecules on the particles, and the magnitude of change in particle electrical parameters.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. An electrorotation device comprising:
a plurality of signal inputs each of said signal inputs receiving a signal which is shifted in phase from signals received by the other signal inputs, wherein each signal input is electrically connected to more than one electrode element, disposed on a single substrate, said electrode elements being organized into a plurality of electrorotation units, each electrorotation unit comprising at least one electrode element electrically connected to each of said signal inputs, wherein the number of electrode elements within each electrorotation unit is the same as the number of signal inputs and wherein when said phase-shifted signals are applied to said electrode elements in said electrorotation units a rotating electric field is produced in said electrorotation units.

2. The electrorotation device of claim 1, wherein the plurality of electrode elements which are electrically connected to each signal input are electrically connected to one another.

3. The electrorotation device of claim 1, wherein said plurality of electrode elements are positioned such that the rotating electrical fields generated by adjacent electrorotation units are in opposite or same directions.

4. The electrorotation device of claim 1, wherein said electrorotation units are disposed on a substrate.

5. The electrorotation device of claim 4, wherein the electrode elements electrically connected to a signal input are electrically insulated from the electrode elements connected to other signal inputs.

6. The electrorotation device of claim 1, wherein said plurality of electrode elements are electrically connected to one another and to each signal input by conductors, and the conductors between electrode elements, which are electrically insulted from one another, are distributed between at least two layers in said substrate.

7. The electrorotation chip of claim 1, wherein said electrode elements are positioned such that an electrode element of a first electrorotation unit is also an electrode element of a second adjacent electrorotation unit.

8. The electrorotation device of claim 1, wherein said phase shifted signals provided by said signal generators may be selectively applied to said electrorotation units.

9. The electrorotation device of claim 1, further comprising switches disposed between said signal generators and said electrode elements such that said phase-shifted signals are applied to said electrode elements in said electrorotation units when said switches are conducting.

10. The electrorotation device of claim 9, wherein said switches are selected from the group consisting of bipolar transistors and metal-oxide-semiconductor-field-effect-transistors (MOSFETs).

11. The electrorotation device of claim 1, wherein a single signal generator generates said plurality of phase-shifted signals which are applied to said signal inputs.

12. The electrorotation device of claim 1, wherein the phase difference between said plurality of phase-shifted signals is 360°/N where N is the number of electrode elements in each electrorotation unit.

\* \* \* \* \*